United States Patent
Parker et al.

(10) Patent No.: US 7,432,284 B2
(45) Date of Patent: Oct. 7, 2008

(54) ESTROGEN RECEPTOR MODULATORS

(75) Inventors: Dann LeRoy Parker, Edison, NJ (US); Robert R. Wilkening, Maplewood, NJ (US); Dongfang Meng, Westfield, NJ (US); Ronald W. Ratcliffe, Matawan, NJ (US)

(73) Assignee: Merck & Co., Inc., Rahway, NJ (US)

( * ) Notice: Subject to any disclaimer, the term of this patent is extended or adjusted under 35 U.S.C. 154(b) by 455 days.

(21) Appl. No.: 10/528,008

(22) PCT Filed: Sep. 15, 2003

(86) PCT No.: PCT/US03/28855

§ 371 (c)(1), (2), (4) Date: Mar. 16, 2005

(87) PCT Pub. No.: WO2004/026887

PCT Pub. Date: Apr. 1, 2004

(65) Prior Publication Data

US 2006/0041003 A1    Feb. 23, 2006

(51) Int. Cl.
- A61K 31/445 (2006.01)
- A61K 31/122 (2006.01)
- C07D 211/06 (2006.01)
- C07C 49/115 (2006.01)

(52) U.S. Cl. .................. 514/325; 546/184; 546/192; 546/195; 546/203; 546/204; 549/200; 549/429; 568/303; 568/308; 568/325; 568/326; 514/315; 514/317; 514/319; 514/675; 514/680

(58) Field of Classification Search .......... 568/303, 568/308, 325, 326; 514/675, 678, 679, 680, 514/315, 325; 546/184, 192, 195, 203, 204; 549/200, 429

See application file for complete search history.

(56) References Cited

U.S. PATENT DOCUMENTS

| 5,891,683 | A | 4/1999 | Usman et al. |
| 6,800,785 | B1 * | 10/2004 | Meng .................. 568/322 |
| 7,087,599 | B2 * | 8/2006 | Parker et al. ........... 514/231.2 |
| 7,151,196 | B2 * | 12/2006 | Wilkening et al. ........ 568/325 |
| 7,157,604 | B2 * | 1/2007 | Meng et al. .............. 564/308 |

FOREIGN PATENT DOCUMENTS

WO    WO 01/82923    11/2001

OTHER PUBLICATIONS

Stetter et al (1984): STN International HCAPLUS database, Columbus (OH), accession No. 1984: 209568.*
Kende et al (1974): STN International HCAPLUS database, Columbus (OH), accession No. 1974: 569342.*
Morimoto, et al. --Journal of American Chem. Society, vol. 124, pp. 3806-3807, 2002.

* cited by examiner

*Primary Examiner*—Golam M Shameem
(74) *Attorney, Agent, or Firm*—Yong Zhao; Valerie J. Camara

(57) ABSTRACT

The present invention relates to compounds and derivatives thereof, their synthesis, and their use as estrogen receptor modulators. The compounds of the instant invention are ligands for estrogen receptors and as such may be useful for treatment or prevention of a variety of conditions related to estrogen functioning including: bone loss, bone fractures, osteoporosis, metastatic bone disease, Pagets disease, periodontal disease, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, and cancer, in particular of the breast, uterus and prostate.

6 Claims, No Drawings

ESTROGEN RECEPTOR MODULATORS

BACKGROUND OF THE INVENTION

Naturally occurring and synthetic estrogens have broad therapeutic utility, including: relief of menopausal symptoms, treatment of acne, treatment of dysmenorrhea and dysfunctional uterine bleeding, treatment of osteoporosis, treatment of hirsutism, treatment of prostatic cancer, treatment of hot flashes and prevention of cardiovascular disease. Because estrogen is very therapeutically valuable, there has been great interest in discovering compounds that mimic estrogen-like behavior in estrogen responsive tissues.

For example, estrogen-like compounds would be beneficial in the treatment and prevention of bone loss. Bone loss occurs in a wide range of subjects, including women that are post-menopausal or have had a hysterectomy, patients who were or are currently being treated with corticosteroids, and patient's having gonadal dysgenesis. The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption, i.e. breakdown, and bone formation, which continues throughout life at the rate of about 14% per year on the average. However, the rate of bone turnover differs from site to site, for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

In the U.S., there are currently about 20 million people with detectable fractures of the vertebrae due to osteoporosis. In addition, there are about 250,000 hip fractures per year attributed to osteoporosis. This clinical situation is associated with a 12% mortality rate within the first two years, while 30% of the patients require nursing home care after the fracture.

Osteoporosis affects approximately 20 to 25 million postmenopausal women in the U.S. alone. It has been theorized that the rapid loss of bone mass in these women is due to the cessation of estrogen production of the ovaries. Since studies have shown that estrogen slows the reduction of bone mass due to osteoporosis, estrogen replacement therapy is a recognized treatment for post-menopausal osteoporosis.

In addition to bone mass, estrogen appears to have an effect on the bioSynthesis of cholesterol and cardiovascular health. Statistically, the rate of occurrence of cardiovascular disease is roughly equal in postmenopausal women and men; however, premenopausal women have a much lower incidence of cardiovascular disease than men. Because postmenopausal women are estrogen deficient, it is believed that estrogen plays a beneficial role in preventing cardiovascular disease. The mechanism is not well understood, but evidence indicates that estrogen can upregulate the low density lipid (LDL) cholesterol receptors in the liver to remove excess cholesterol.

Postmenopausal women given estrogen replacement therapy experience a return of lipid levels to concentrations comparable to levels associated with the premenopausal state. Thus, estrogen replacement therapy could be an effective treatment for such disease. However, the side effects associated with long term estrogen use limit the use of this alternative.

Also, the estrogen receptor ligands of the present invention can have utility as an anti-depressant, especially when the depression results from an estrogen deficiency.

In models, estrogen has been shown to have beneficial effects on cognitive functioning, such as relieveing anxiety and depression and treating and/or preventing Alzheimer's disease. Estrogen affects the central nervous system by increasing cholinergic functioning, neurotrophin and neurotrophin receptor expression. Estrogen also increases glutamergic synaptic transmission, alters amyloid precursor protein processing and provides neuroprotection. Thus, the estrogen receptor modulators of the present invention could be beneficial for improving cognitive functioning or treating mild cognitive impairment, attention deficit disorder, sleep disorders, irritability, impulsivity, anger management, multiple sclerosis and Parkinsons disease. See, Sawada, H and Shimohama, S, "Estrogens and Parkinson disease: novel approach for neuroprotection," *Endocrine.* 2003 June; 21(1): 77-9; McCullough L D, and Hurn, P D, "Estrogen and ischemic neuroprotection: an integrated view," *Trends Endocrinol Metab.* 2003 July; 14(5):228-35; which are hereby incorporated by reference in their entirety.

The estrogen receptor has been found to have two forms: ERα and ERβ. Ligands bind differently to these two forms, and each form has a different tissue specificity to binding ligands. Thus, it is possible to have compounds that are selective for ERα or ERβ, and therefore confer a degree of tissue specificity to a particular ligand.

Specifically, estrogen receptor beta (ERβ) selective agonists would be useful in the treatment of anxiety and/or depressive illness, including depression, perimenopausal depression, post-partum depression, premenstrual syndrome, manic depression, anxiety, dementia, and obsessive compulsive behavior, as either a single agent or in combination with other agents. Clinical studies have demonstrated the efficacy of the natural estrogen, 17β-estradiol, for the treatment of various forms of depressive illness, see Schmidt P J, Nieman L, Danaceau M A, Tobin M B, Roca C A, Murphy J H, Rubinow D R. Estrogen replacement in perimenopause-related depression: a preliminary report. *Am J Obstet Gynecol* 183:414-20, 2000; and Soares C N, Almeida O P, Joffe H, Cohen L S. Efficacy of estradiol for the treatment of depressive disorders in perimenopausal women: a double-blind, randomized, placebo-controlled trial. *Arch Gen Psychiatry.* 58:537-8, 2001; which are hereby incorporated by reference. Bethea et al (Lu N Z, Shlaes T A, Gundlah C, Dziennis S E, Lyle R E, Bethea C L. Ovarian steroid action on tryptophan hydroxylase protein and serotonin compared to localization of ovarian steroid receptors in midbrain of guinea pigs. *Endocrine* 11:257-67, 1999, which is hereby incorporated by reference) have suggested that the anti-depressant activity of estrogen may be mediated via regulation of serotonin synthesis in the serotonin containing cells concentrated in the dorsal raphe nucleus.

It is believed by some in the field that the physiological responses to estrogen are generally mediated via a series of biochemical events initiated by a selective, high affinity interaction between estrogen and an estrogen receptor. There are two estrogen receptors, ERα and ERβ, and there is co-localization of ERβ (and not ERα) in the serotonin containing cells of the rodent raphe nucleus. Using ERβ selective compounds, estrogen increases transcription of the tryptophan hydroxylase gene (TPH, the key enzyme in serotonin synthesis) via an ERα mediated event. Potential ERβ selective agonists can be tested in a rodent model of depression by methods familiar to those skilled in the art, for example in a forced swim assay. Likewise, potential ERβ selective agonists can be tested in a rodent model of anxiety by methods familiar to those skilled in the art, for example a guinea pig pup vocalization assay and the resident intruder assay.

Other disease states that affect postmenopausal women include estrogen-dependent breast cancer and uterine cancer. Anti-estrogen compounds, such as tamoxifen, have commonly been used as chemotherapy to treat breast cancer patients. Tamoxifen, a dual antagonist and agonist of estrogen receptors, is beneficial in treating estrogen-dependent breast cancer. However, treatment with tamoxifen is less than ideal because tamoxifen's agonist behavior enhances its unwanted estrogenic side effects. For example, tamoxifen and other compounds that agonize estrogen receptors tend to increase cancer cell production in the uterus. A better therapy for such cancers would be an anti-estrogen compound that has negligible or nonexistent agonist properties.

Although estrogen can be beneficial for treating pathologies such as bone loss, increased lipid levels, and cancer, long-term estrogen therapy has been implicated in a variety of disorders, including an increase in the risk of uterine and endometrial cancers. These and other side effects of estrogen replacement therapy are not acceptable to many women, thus limiting its use.

Alternative regimens, such as a combined progestogen and estrogen dose, have been suggested in an attempt to lessen the risk of cancer. However, such regimens cause the patient to experience withdrawal bleeding, which is unacceptable to many older women. Furthermore, combining estrogen with progestogen reduces the beneficial cholesterol-lowering effect of estrogen therapy. In addition, the long term effects of progestogen treatment are unknown.

In addition to post-menopausal women, men suffering from prostatic cancer can also benefit from anti-estrogen compounds. Prostatic cancer is often endocrine-sensitive; androgen stimulation fosters tumor growth, while androgen suppression retards tumor growth. The administration of estrogen is helpful in the treatment and control of prostatic cancer because estrogen administration lowers the level of gonadotropin and, consequently, androgen levels.

What is needed in the art are compounds that can produce the same positive responses as estrogen replacement therapy without the negative side effects. Also needed are estrogen-like compounds that exert selective effects on different tissues of the body.

The compounds of the instant invention are ligands for estrogen receptors and as such may be useful for treatment or prevention of a variety of conditions related to estrogen functioning including: bone loss, bone fractures, osteoporosis, metastatic bone disease, Paget's disease, periodontal disease, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, anxiety, depression resulting from an estrogen deficiency, and cancer, in particular of the breast, uterus and prostate.

SUMMARY OF THE INVENTION

The present invention relates to compounds that are capable of treating and/or preventing a variety of conditions related to estrogen functioning. One embodiment of the present invention is illustrated by a compound of Formula I, and the pharmaceutically acceptable salts and stereoisomers thereof:

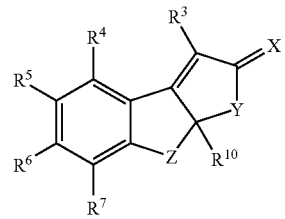

DETAILED DESCRIPTION OF THE INVENTION

The present invention relates to compounds useful as estrogen receptor modulators. Compounds of the present invention are described by the following chemical formula:

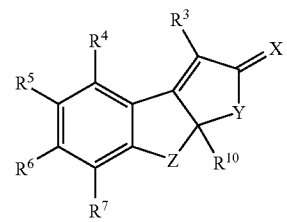

wherein X is O, N—$OR^a$, N—$NR^aR^b$ or $C_{1-6}$ alkylidene, wherein said alkylidene group is unsubstituted or substituted with a group selected from hydroxy, amino, O($C_{1-4}$alkyl), NH($C_{1-4}$alkyl), or N($C_{1-4}$alkyl)$_2$, or X represents the following two singly bonded substituents, H and $OR^a$;

Y is $CR^1R^2$, $CH_2CR^1R^2$, $CH_2CH_2CR^1R^2$ or $CH_2CR^1R^2CH_2$;

Z is $CR^8R^9$, $CR^8R^9CH_2$ or $CR^{11}=CR^{12}$, and with the proviso that Y can not be $CH_2CR^1R^2$ when Z is $CR^8R^9$;

$R^1$ is hydrogen, $C_{1-6}$alkyl, $C_{2-6}$alkenyl or $C_{2-6}$alkynyl, wherein said alkyl, alkenyl and alkynyl groups are either unsubstituted or substituted with a group selected from $OR^c$, $SR^c$, $NR^bR^c$, C(=O)$R^c$, C(=O)$CH_2$OH, or phenyl, wherein said phenyl group can either be unsubstituted or substituted with 1-3 substituents independently selected from $C_{1-4}$alkyl, OH, O($C_{1-4}$alkyl), $NH_2$, NH($C_{1-4}$alkyl), N($C_{1-4}$alkyl)$_2$, halo, CN, $NO_2$, $CO_2$H, $CO_2$($C_{1-4}$alkyl), C(O)H or C(O)($C_{1-4}$alkyl);

$R^2$ is hydrogen, hydroxy, iodo, O(C=O)$R^c$, C(=O)$R^c$, $CO_2R^c$, $C_{1-6}$alkyl, $C_{2-6}$alkenyl or $C_{2-6}$alkynyl, wherein said alkyl, alkenyl and alkynyl groups are either unsubstituted or substituted with a group selected from $OR^c$, $SR^c$, $NR^bR^c$, C(=O)$R^c$, C(=O)$CH_2$OH, or phenyl, wherein said phenyl group can either be unsubstituted or substituted with 1-3 substituents independently selected from $C_{1-4}$alkyl, OH, O($C_{1-4}$alkyl), $NH_2$, NH($C_{1-4}$alkyl), N($C_{1-4}$alkyl)$_2$, halo, CN, $NO_2$, $CO_2$H, $CO_2$($C_{1-4}$alkyl), C(O)H or C(O)($C_{1-4}$alkyl);

or $R^1$ and $R^2$, when taken together with the carbon atom to which they are attached, form a carbonyl group;

or $R^1$ and $R^2$, when taken together, form a $C_{1-6}$ alkylidene group, wherein said alkylidene group is either unsubstituted or substituted with a group selected from hydroxy, O($C_{1-4}$alkyl), N($C_{1-4}$alkyl)$_2$ or phenyl, wherein said phenyl group can either be unsubstituted or substituted with 1-3 substituents independently selected from $C_{1-4}$alkyl, OH, O($C_{1-4}$alkyl), $NH_2$, NH($C_{1-4}$alkyl), NH($C_{1-4}$alkyl)$_2$, halo, CN, $NO_2$, $CO_2H$, $CO_2$($C_{1-4}$alkyl), C(O)H or C(O)($C_{1-4}$alkyl);

$R^3$ is hydrogen, fluoro, chloro, bromo, iodo, cyano, nitro, $NR^aR^c$, $OR^a$, C(=O)$R^a$, $CO_2R^c$, $CONR^aR^c$, $SR^a$, S(=O)$R^a$, $SO_2R^a$, $C_{1-10}$alkyl, $C_{2-10}$alkenyl, $C_{2-10}$alkynyl, $C_{3-7}$cycloalkyl, $C_{5-7}$cycloalkenyl, 4-7 membered heterocycloalkyl, (cycloalkyl)alkyl, (heterocycloalkyl)alkyl, aryl, heteroaryl, arylalkyl or (heteroaryl)alkyl, wherein said alkyl, alkenyl, alkynyl, cycloalkyl, cycloalkenyl, aryl and heteroaryl groups are either unsubstituted or independently substituted with 1, 2 or 3 groups selected from fluoro, chloro, bromo, iodo, cyano, $OR^a$, $NR^aR^c$, O(C=O)$R^a$, O(C=O)$NR^aR^c$, $NR^a$(C=O)$R^c$, $NR^a$(C=O)$OR^c$, C(=O)$R^a$, $CO_2R^a$, $CONR^aR^c$, $CSNR^aR^c$, $SR^a$, S(O)$R^a$, $SO_2R^a$, $SO_2NR^aR^c$, $LR^d$ or $MLR^d$;

$R^4$ is hydrogen, hydroxy or fluoro;

$R^5$ is hydrogen, hydroxy, amino, methyl, $CF_3$, fluoro, chloro or bromo;

$R^6$ is hydrogen, fluoro, chloro, methyl, amino, $OR^a$, $OR^b$, O(C=O)$R^c$, O(C=O)$OR^c$, NH(C=O)$R^e$ or NH(C=O)$OR^e$;

$R^7$ is hydrogen, $OR^b$, $NR^bR^c$, fluoro, chloro, bromo, iodo, cyano, nitro, $C_{1-6}$alkyl, $C_{2-6}$alkenyl, $CF_3$ or $CHF_2$;

$R^8$ and $R^9$ are each independently selected from hydrogen, fluoro, chloro, $C_{1-6}$alkyl, $C_{2-6}$alkenyl or $C_{2-6}$alkynyl, or $R^8$ and $R^9$, when taken together with the carbon atom to which they are attached, form a 3-5 membered cycloalkyl ring, or $R^8$ and $R^9$, when taken together with the carbon atom to which they are attached, form a carbonyl group;

$R^{10}$ is hydrogen, $C_{1-10}$alkyl, $C_{2-10}$alkenyl, $C_{2-10}$alkynyl, $C_{3-6}$cycloalkyl, C4-6cycloalkenyl, (cycloalkyl)alkyl, (cycloalkyl)alkenyl, (cycloalkenyl)alkyl, aryl, heteroaryl, arylalkyl or (heteroaryl)alkyl, wherein said alkyl, alkenyl, alkynyl, cycloalkyl, cycloalkenyl, (cycloalkyl)alkyl, (cycloalkyl)alkenyl, (cycloalkenyl)alkyl, aryl, heteroaryl, arylalkyl and (heteroaryl)alkyl groups are optionally substituted with a group selected from bromo, iodo, cyano, $OR^b$, $SR^b$, C(=O)$R^b$, 1-3 $C_{1-3}$alkyl, 1-3 chloro or 1-5 fluoro, or $R^{10}$ and $R^1$, when taken together with the two to four intervening carbon atoms to which they are attached, form a 5-6 membered cycloalkyl or cycloalkenyl ring which is optionally substituted with 1-3 groups independently selected from oxo, hydroxy, fluoro, chloro, $C_{1-6}$alkyl, $C_{2-6}$alkenyl, $C_{2-6}$alkynyl, $C_{1-6}$alkylidenyl, $C_{3-6}$cycloalkyl, (cycloalkyl)alkyl, phenyl, or phenylalkyl, wherein said alkyl, alkenyl, alkynyl, alkylidenyl, cycloalkyl, (cycloalkyl)alkyl, phenyl, and phenylalkyl groups are optionally substituted with a group selected from chloro, bromo, iodo, $OR^b$, $SR^b$, $C_{1-3}$alkyl, C(=O)$R^b$, or 1-5 fluoro;

$R^{11}$ is hydrogen, fluoro and $C_{1-4}$alkyl;

$R^{12}$ is hydrogen, fluoro and $C_{1-4}$alkyl;

$R^a$ is hydrogen, $C_{1-10}$alkyl, and phenyl, wherein said alkyl group is optionally substituted with a group selected from hydroxy, amino, O($C_{1-4}$alkyl), NH($C_{1-4}$alkyl), N($C_{1-4}$alkyl)$_2$, phenyl, or 1-5 fluoro, and wherein said phenyl groups can either be unsubstituted or substituted with 1-3 substituents independently selected from $C_{1-4}$alkyl, OH, O($C_{1-4}$alkyl), $NH_2$, NH($C_{1-4}$alkyl), N($C_{1-4}$alkyl)$_2$, halo, CN, $NO_2$, $CO_2H$, $CO_2$($C_{1-4}$alkyl), C(O)H or C(O)($C_{1-4}$alkyl);

$R^b$ is hydrogen, $C_{1-10}$alkyl, benzyl or phenyl, wherein said phenyl group can either be unsubstituted or substituted with 1-3 substituents independently selected from $C_{1-4}$alkyl, OH, O($C_{1-4}$alkyl), $NH_2$, NH($C_{1-4}$alkyl), N($C_{1-4}$alkyl)$_2$, halo, CN, $NO_2$, $CO_2H$, $CO_2$($C_{1-4}$alkyl), C(O)H or C(O)($C_{1-4}$alkyl);

$R^c$ is hydrogen, $C_{1-10}$alkyl or phenyl, wherein said phenyl group can either be unsubstituted or substituted with 1-3 substituents independently selected from $C_{1-4}$alkyl, OH, O($C_{1-4}$alkyl), $NH_2$, NH($C_{1-4}$alkyl), N($C_{1-4}$alkyl)$_2$, halo, CN, $NO_2$, $CO_2H$, $CO_2$($C_{1-4}$alkyl), C(O)H or C(O)($C_{1-4}$alkyl);

or $R^a$ and $R^c$, whether or not on the same atom, can be taken together with any attached and intervening atoms to form a 4-7 membered ring;

$R^d$ is $NR^bR^c$, $OR^a$, $CO_2R^a$, O(C=O)$R^a$, CN, $NR^c$(C=O)$R^b$, $CONR^aR^c$, $SO_2NR^aR^c$ or a 4-9 membered mono- or bicyclic N-heterocycloalkyl ring that can be optonally substituted with 1-3 $C_{1-3}$ alkyl and can be optionally interrupted by O, S, $NR^c$, or C=O;

$R^e$ is hydrogen, $C_{1-6}$alkyl, $C_{2-6}$alkenyl, phenyl or phenylalkyl, wherein said alkyl, alkenyl, or phenyl group can either be unsubstituted or substituted with 1-3 substituents independently selected from $C_{1-3}$alkyl, OH, O($C_{1-4}$alkyl), $NH_2$, NH($C_{1-4}$alkyl), N($C_{1-4}$alkyl)$_2$, halo, CN, $NO_2$, $CO_2H$, $CO_2$($C_{1-4}$alkyl), C(O)H or C(O)($C_{1-4}$alkyl);

L is $CR^bR^c$, $C_{2-6}$ alkylene or $C_{2-6}$ alkenylene, wherein said alkylene and alkenylene linkers can be optionally interrupted by O, S, or $NR^c$;

M is O, S, $NR^c$, C=O, O(C=O), (C=O)O, $NR^c$(C=O) or (C=O)$NR^c$;

or a pharmaceutically acceptable salt thereof.

In a class of the invention, X is selected from O and N—$OR^a$. In a subclass of the invention, X is selected from O and N—OH. In a further subclass of the invention, X is O.

In a class of the invention, Y is selected from $CR^1R^2$, $CH_2CR^1R^2$, and $CH_2CH_2CR^1R^2$. In a subclass of the invention, Y is selected from $CR^1R^2$ and $CH_2CH_2CR^1R^2$. In a further subclass of the invention, Y is selected from $CH_2$ and $CH_2CH_2CH_2$.

In a class of the invention, Z is selected from $CR^8R^9$ and $CH_2CH_2$, with the proviso that Y can not be $CH_2R^1R^2$ when Z is $CR^8R^9$. In a subclass of the invention, Z is selected from $CH_2$ and $CH_2CH_2$, with the proviso that Y can not be $CH^2CR^1R^2$ when Z is $CH_2$.

In a class of the invention, $R^1$ is selected from hydrogen and $C_{1-6}$alkyl, wherein said group is either unsubstituted or substituted with a group selected from $OR^c$ or C(=O)$R^c$. In a subclass of the invention, $R^1$ is selected from hydrogen and $C_{1-3}$alkyl.

In a class of the invention, $R^2$ is selected from hydrogen, hydroxy, and $C_{1-6}$alkyl, wherein said alkyl group is either unsubstituted or substituted with a group selected from $OR^{c \text{ or } C(=O)Rc}$. In a subclass of the invention, $R^2$ is selected from hydrogen, hydroxy, and $C_{1-3}$alkyl.

In a class of the invention, $R^3$ is selected from chloro, bromo, iodo, cyano, $CO_2R^c$, $C_{1-10}$alkyl, $C_{3-7}$cycloalkyl, aryl and heteroaryl, wherein said alkyl, cycloalkyl, aryl and heteroaryl groups are either unsubstituted or independently substituted with 1, 2 or 3 groups selected from fluoro, chloro, bromo, cyano, $OR^a$, $CO_2R^a$, $LR^d$, and $MLR^d$. In a subclass of the invention, $R^3$ is selected from chloro, bromo, cyano, $C_{1-10}$alkyl, $C_{3-7}$cycloalkyl, aryl, and heteroaryl, wherein said alkyl, cycloalkyl, aryl, and heteroaryl groups are either unsubstituted or independently substituted with 1, 2 or 3 groups selected from fluoro, chloro, cyano, $OR^a$, $LR^d$, and $MLR^d$. In a further subclass of the invention, $R^3$ is selected from chloro, bromo, cyano, methyl, ethyl, trifluoromethyl, cyclopropyl, phenyl, furyl, and thienyl.

In a class of the invention, $R^4$ is selected from hydrogen and fluoro. In a subclass of the invention, $R^4$ is hydrogen.

In a class of the invention, $R^5$ is selected from hydrogen, hydroxy, fluoro, chloro, and bromo. In a subclass of the invention, $R^5$ is selected from hydrogen and fluoro.

In a class of the invention, $R^6$ is selected from hydrogen, fluoro, amino, $OR^a$, and $O(C=O)R^c$. In a subclass of the invention, $R^6$ is selected from $OR^a$ and $O(C=O)R^c$. In a further subclass of the invention, $R^6$ is hydroxy.

In a class of the invention, $R^7$ is selected from hydrogen, fluoro, chloro, bromo, and $C_{1-6}$alkyl. In a subclass of the invention, $R^7$ is selected from hydrogen, chloro, and methyl.

In a class of the invention, $R^8$ and $R^9$ are each independently selected from hydrogen, fluoro, chloro, and $C_{1-6}$alkyl, or $R^8$ and $R^9$, when taken together with the carbon atom to which they are attached, form a carbonyl group. In a subclass of the invention, $R^8$ and $R^9$ are each hydrogen or $R^8$ and $R^9$, when taken together with the carbon atom to which they are attached, form a carbonyl group. In a further subclass of the invention, $R^8$ and $R^9$ are each hydrogen.

In a class of the invention, $R^{10}$ is selected from $C_{1-10}$alkyl, $C_{2-10}$alkenyl, $C_{3-6}$cycloalkyl, and (cycloalkyl)alkyl, wherein said alkyl, alkenyl, cycloalkyl, and (cycloalkyl)alkyl groups are optionally substituted with a group selected from bromo, $SR^b$, 1-3 chloro, or 1-5 fluoro. In a subclass of the invention, $R^{10}$ is selected from $C_{1-10}$alkyl and (cycloalkyl)alkyl, wherein said alkyl and (cycloalkyl)alkyl groups are unsubstituted or substituted with 1-5 fluoro.

Non-limiting examples of the present invention include, but are not limited to:

3-bromo-8a-butyl-6-hydroxy-8,8a-dihydrocyclopenta[a]inden-2(1H)-one;
(rac)-(1S,8aR)-3-bromo-8a-butyl-6-hydroxy-1-propyl-8,8a-dihydrocyclopenta[a]inden-2(1H)-one;
1,3a-diethyl-7-hydroxy-3,3a,4,5-tetrahydro-2H-cyclopenta[a]naphthalen-2-one;
3a-butyl-7-hydroxy-3,3a,4,5-tetrahydro-2H-cyclopenta[a]naphthalen-2-one;
1,6-dibromo-3a-butyl-7-hydroxy-3,3a,4,5-tetrahydro-2H-cyclopenta[a]naphthalen-2-one;
1-bromo-3a-butyl-7-hydroxy-3,3a,4,5-tetrahydro-2H-cyclopenta[a]naphthalen-2-one;
6-bromo-3a-butyl-7-hydroxy-1-methyl-3,3a,4,5-tetrahydro-2H-cyclopenta[a]naphthalen-2-one;
3a-butyl-7-hydroxy-1,6-dimethyl-3,3a,4,5-tetrahydro-2H-cyclopenta[a]naphthalen-2-one;
3a-butyl-7-hydroxy-1-methyl-3,3a,4,5-tetrahydro-2H-cyclopenta[a]naphthalen-2-one;
1-bromo-3a-butyl-6-chloro-8-fluoro-7-hydroxy-3,3a,4,5-tetrahydro-2H-cyclopenta[a]naphthalen-2-one;
10a-butyl-7-hydroxy-1,9,10,10a-tetrahydro-3(2H)-phenanthrenone;
4-bromo-10a-butyl-7-hydroxy-1,9,10,10a-tetrahydro-3(2H)-phenanthrenone;
9a-butyl-2-hydroxy-5-methyl-8,9,9a,10-tetrahydrobenzo[a]azulen-6(7H)-one;
1-bromo-7-hydroxy-3a-methyl-3,3a,4,5-tetrahydro-2H-cyclopenta[a]naphthalen-2-one;
7-hydroxy-1,3a-dimethyl-3,3a,4,5-tetrahydro-2H-cyclopenta[a]naphthalen-2-one;
1,6-dibromo-7-hydroxy-3a-methyl-3,3a,4,5-tetrahydro-2H-cyclopenta[a]naphthalen-2-one;
6-bromo-7-hydroxy-1,3a-dimethyl-3,3a,4,5-tetrahydro-2H-cyclopenta[a]naphthalen-2-one;
1-bromo-3a-ethyl-7-hydroxy-3,3a,4,5-tetrahydro-2H-cyclopenta[a]naphthalen-2-one;
3a-ethyl-7-hydroxy-1-methyl-3,3a,4,5-tetrahydro-2H-cyclopenta[a]naphthalen-2-one;
1,6-dibromo-3a-ethyl-7-hydroxy-3,3a,4,5-tetrahydro-2H-cyclopenta[a]naphthalen-2-one;
1-bromo-7-hydroxy-3a-propyl-3,3a,4,5-tetrahydro-2H-cyclopenta[a]naphthalen-2-one;
7-hydroxy-1-methyl-3a-propyl-3,3a,4,5-tetrahydro-2H-cyclopenta[a]naphthalen-2-one;
1,6-dibromo-7-hydroxy-3a-propyl-3,3a,4,5-tetrahydro-2H-cyclopenta[a]naphthalen-2-one;
1-bromo-6-chloro-3a-ethyl-7-hydroxy-3,3a,4,5-tetrahydro-2H-cyclopenta[a]naphthalen-2-one;
1-bromo-3a-butyl-6-chloro-7-hydroxy-3,3a,4,5-tetrahydro-2H-cyclopenta[a]naphthalen-2-one;

and the pharmaceutically acceptable salts thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. The present invention also relates to methods for making the pharmaceutical compositions of the present invention. The present invention is also related to processes and intermediates useful for making the compounds and pharmaceutical compositions of the present invention. These and other aspects of the invention will be apparent from the teachings contained herein.

Utilities

The compounds of the present invention are selective modulators of estrogen receptors and are therefore useful to treat or prevent a variety of diseases and conditions related to estrogen receptor functioning in mammals, preferably humans.

A variety of diseases and conditions related to estrogen receptor functioning includes, but is not limited to, bone loss, bone fractures, osteoporosis, metastatic bone disease, Paget's disease, periodontal disease, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, anxiety, depression resulting from an estrogen deficiency, and cancer, in particular of the breast, uterus and prostate. In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

The present invention also relates to methods for eliciting an estrogen receptor modulating effect in a mammal in need thereof by administering the compounds and pharmaceutical compositions of the present invention.

The present invention also relates to methods for eliciting an estrogen receptor antagonizing effect in a mammal in need thereof by administering the compounds and pharmaceutical compositions of the present invention. The estrogen receptor antagonizing effect can be either an ERα antagonizing effect, an ERβ antagonizing effect or a mixed ERα and ERβ antagonizing effect.

The present invention also relates to methods for eliciting an estrogen receptor agonizing effect in a mammal in need thereof by administering the compounds and pharmaceutical compositions of the present invention. The estrogen receptor agonizing effect can be either an ERα agonizing effect, an ERβ agonizing effect or a mixed ERα and ERβ agonizing effect. A preferred method of the present invention is eliciting an ERβ agonizing effect.

The present invention also relates to methods for treating or preventing disorders related to estrogen functioning, bone loss, bone fractures, osteoporosis, metastatic bone disease, Paget's disease, periodontal disease, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, anxiety, depression resulting from an estrogen deficiency, and cancer, in particular of the breast, uterus and prostate in a mammal in need thereof by administering the compounds and pharmaceutical compositions of the present invention. Exemplifying the invention is a method of treating or preventing depression. Exemplifying the invention is a method of treating or preventing anxiety. Exemplifying the invention is a method of treating or preventing hot flashes. Exemplifying the invention is a method of treating or preventing cancer. Exemplifying the invention is a method of treating or preventing cardiovascular disease.

An embodiment of the invention is a method for treating or preventing cancer, especially of the breast, uterus or prostate, in a mammal in need thereof by administering the compounds and pharmaceutical compositions of the present invention. The utility of SERMs for the treatment of breast, uterine or prostate cancer is known in the literature, see T. J. Powles, "Breast cancer prevention," Oncologist 2002; 7(1):60-4; Park, W. C. and Jordan, V. C., "Selective estrogen receptor modulators (SERMS) and their roles in breast cancer prevention." Trends Mol Med. 2002 February; 8(2):82-8; Wolff, A. C. et al., "Use of SERMs for the adjuvant therapy of early-stage breast cancer," Ann N Y Acad. Sci. 2001 December; 949:80-8; Steiner, M. S. et al., "Selective estrogen receptor modulators for the chemoprevention of prostate cancer," Urology 2001 April; 57(4 Suppl 1):68-72.

Another embodiment of the invention is a method of treating or preventing metastatic bone disease in a mammal in need thereof by administering to the mammal a therapeutically effective amount of any of the compounds or pharmaceutical compositions described above. The utility of SERMS in the treatment of metastatic bone disease is known in the literature, see, Campisi, C. et al., "Complete resoultion of breast cancer bone metastasis through the use of beta-interferon and tamoxifen," Eur J Gynaecol Oncol 1993; 14(6): 479-83.

Another embodiment of the invention is a method of treating or preventing gynecomastia in a mammal in need thereof by administering to the mammal a therapeutically effective amount of any of the compounds or pharmaceutical compositions described above. The utility of SERMS in the treatment of gynecomastia is known in the literature, see, Ribeiro, G. and Swindell R., "Adjuvant tamoxifen for male breast cancer." Br J Cancer 1992; 65:252-254; Donegan, W., "Cancer of the Male Breast," JGSM Vol. 3, Issue 4, 2000.

Another embodiment of the invention is a method of treating or preventing post-menopausal osteoporosis, glucocorticoid osteoporosis, hypercalcemia of malignancy, bone loss and bone fractures in a mammal in need thereof by administering to the mammal a therapeutically effective amount of any of the compounds or pharmaceutical compositions described above. The utility of SERMs to treat or prevent osteoporosis, hypercalcemia of malignancy, bone loss or bone fractures is known in the literature, see Jordan, V. C. et al., "Selective estrogen receptor modulation and reduction in risk of breast cancer, osteoporosis and coronary heart disease," Natl Cancer Inst 2001 October; 93(19):1449-57; Bjarnason, N H et al., "Six and twelve month changes in bone turnover are realted to reduction in vertebral fracture risk during 3 years of raloxifene treatment in postemenopausal osteoporosis," Osteoporosis Int 2001; 12(11):922-3; Fentiman I. S., "Tamoxifen protects against steroid-induced bone loss," Eur J Cancer 28:684-685 (1992); Rodan, G. A. et al., "Therapeutic Approaches to Bone Diseases," Science Vol 289, 1 Sep. 2000.

Another embodiment of the invention is a method of treating of preventing periodontal disease or tooth loss in a mammal in need thereof by administering to the mammal a therapeutically effective amount of any of the compounds or pharmaceutical compositions described above. The use of SERMs to treat periodontal disease or tooth loss in a mammal is known in the literature, see Rodan, G. A. et al., "Therapeutic Approaches to Bone Diseases," Science Vol 289, 1 Sep. 2000 pp. 1508-14.

Another embodiment of the invention is a method of treating of preventing Paget's disease in a mammal in need thereof by administering to the mammal a therapeutically effective amount of any of the compounds or pharmaceutical compositions described above. The use of SERMs to treat Paget's disease in a mammal is known in the literature, see Rodan, G. A. et al., "Therapeutic Approaches to Bone Diseases," Science Vol 289, 1 Sep. 2000 pp. 1508-14.

Another embodiment of the invention is a method of treating or preventing uterine fibroid disease in a mammal in need thereof by administering to the mammal a therapeutically effective amount of any of the compounds or pharmaceutical compositions described above. The use of SERMS to treat uterine fibroids, or uterine leiomyomas, is known in the literature, see Palomba, S., et al, "Effects of raloxifene treatment on uterine leiomyomas in postmenopausal women," Fertil Steril. 2001 July; 76(1):38-43.

Another embodiment of the invention is a method of treating or preventing obesity in a mammal in need thereof by administering to the mammal a therapeutically effective amount of any of the compounds or pharmaceutical compositions described above. The use of SERMs to treat obesity is known in the literature, see Picard, F. et al., "Effects of the estrogen antagonist EM-652.HCl on energy balance and lipid metabolism in ovariectomized rats," Int J Obes Relat Metab Disord. 2000 July; 24(7):830-40.

Another embodiment of the invention is a method of treating or preventing cartilage degeneration, rheumatoid arthritis or osteoarthritis in a mammal in need thereof by administering to the mammal a therapeutically effective amount of any of the compounds or pharmaceutical-compositions described above. The use of SERMs to treat cartilage degeneration, rheumatoid arthritis or osteoarthritis is known in the literature, see Badger, A. M. et al., "Idoxifene, a novel selective estrogen receptor modulator, is effective in a rat model of adjuvant-induced arthritis." J Pharmacol Exp Ther. 1999 December; 291(3):1380-6.

Another embodiment of the invention is a method of treating or preventing endometriosis in a mammal in need thereof by administering to the mammal a therapeutically effective amount of any of the compounds or pharmaceutical compositions described above. The use of SERMs to treat endometriosis is known in the art, see Steven R. Goldstein, "The Effect of SERMs on the Endometrium," Annals of the New York Academy of Sciences 949:237-242 (2001).

Another embodiment of the invention is a method of treating or preventing urinary incontinence in a mammal in need thereof by administering to the mammal a therapeutically effective amount of any of the compounds or pharmaceutical compositions described above. The use of SERMs to treat urinary incontinence is known in the art, see, Goldstein, S. R., "Raloxifene effect on frequency of surgery for pelvic floor relaxation," Obstet Gynecol. 2001 July; 98(1):91-6.

Another embodiment of the invention is a method of treating or preventing cardiovascular disease, restenosis, lowering levels of LDL cholesterol and inhibiting vascular smooth muscle cell proliferation in a mammal in need thereof by administering to the mammal a therapeutically effective amount of any of the compounds or pharmaceutical compositions described above. The utility of SERMs in treating or preventing cardiovascular disease, restenosis, lowering levels of LDL cholesterol and inhibiting vascular smooth muscle cell proliferation is known in the art, see Nuttall, M E et al., "Idoxifene: a novel selective estrogen receptor modulator prevents bone loss and lowers cholesterol levels in ovariectomized rats and decreases uterine weight in intact rats," Endocrinology 1998 December; 139(12):5224-34; Jordan, V. C. et al., "Selective estrogen receptor modulation and reduction in risk of breast cancer, osteoporosis and coronary heart disease," Natl Cancer Inst 2001 October; 93(19):1449-57; Guzzo J A., "Selective estrogen receptor modulators—a new age of estrogens in cardiovascular disease?," Clin Cardiol 2000 January; 23(1):15-7; Simoncini T, Genazzani A R., "Direct vascular effects of estrogens and selective estrogen receptor modulators," Curr Opin Obstet Gynecol 2000 June; 12(3):181-7.

Another embodiment of the invention is a method of treating or preventing the impairment of cognitive functioning or cerebral degenerative disorders in a mammal in need thereof by administering to the mammal a therapeutically effective amount of any of the compounds or pharmaceutical compositions described above. The utility of SERMs to prevent the impairment of cognitive functioning is known in the art, see Yaffe, K., K. Krueger, S. Sarkar, et al. 2001. Cognitive function in postmenopausal women treated with raloxifene. N. Eng. J. Med. 344: 1207-1213.

Another embodiment of the invention is a method of treating or preventing depression in a mammal in need thereof by administering to the mammal a therapeutically effective amount of any of the compounds or pharmaceutical compositions described above. The utility of estrogens to prevent depression has been described in the art, see Carranza-Liram S., Valentino-Figueroa M L, "Estrogen therapy for depression in postmenopausal women." Int J Gynnaecol Obstet 1999 April; 65(1):35-8.

Another embodiment of the invention is a method of treating or preventing anxiety in a mammal in need thereof by administering to the mammal a therapeutically effective amount of any of the compounds or pharmaceutical compositions described above. The contribution of estrogen receptors in the modulation of emotional processes, such as anxiety has been described in the art, see Krezel, W., et al., "Increased anxiety and synaptic plasticity in estrogen receptor beta-deficient mice." Proc Natl Acad Sci USA 2001 Oct. 9; 98 (21): 12278-82.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to estrogen functioning.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

In the case of tablets for oral use, carriers which are commonly used include lactose and corn starch, and lubricating agents, such as magnesium stearate, are commonly added. For oral administration in capsule form, useful diluents include lactose and dried corn starch. For oral use of a therapeutic compound according to this invention, the selected compound may be administered, for example, in the form of tablets or capsules, or as an aqueous solution or suspension. For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any, oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The instant compounds are also useful in combination with known agents useful for treating or preventing bone loss, bone fractures, osteoporosis, metastatic bone disease, Paget's disease, periodontal disease, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, anxiety, depression resulting from an estrogen deficiency, and cancer, in particular of the breast, uterus and prostate. Combinations of the presently disclosed compounds with other agents useful in treating or preventing the disorders disclosed herein are within the scope of the invention. A person of ordinary skill in the art would be able to discern which combinations of agents would be useful based on the particular characteristics of the drugs and the disease involved. Such agents include the following: an organic bisphosphonate; a cathepsin K inhibitor; an estrogen or an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; calcitonin; Vitamin D or a synthetic Vitamin D analogue; selective serotonin reuptake inhibitors (SSRIs); and the pharmaceutically acceptable salts and mixtures thereof. A preferred combination is a compound of the present invention and an organic bisphosphonate. Another preferred combination is a compound of the present invention and a cathepsin K inhibitor. Another preferred combination is a compound of the present invention and an estrogen. Another preferred combination is a compound of the present invention and an androgen receptor modulator. Another preferred combination is a compound of the present invention and an osteoblast anabolic agent.

"Organic bisphosphonate" includes, but is not limited to, compounds of the chemical formula

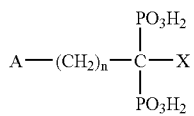

wherein n is an integer from 0 to 7 and wherein A and X are independently selected from the group consisting of H, OH, halogen, $NH_2$, SH, phenyl, $C_{1-30}$ alkyl, $C_{3-30}$ branched or cycloalkyl, bicyclic ring structure containing two or three N, $C_{1-30}$ substituted alkyl, $C_{1-10}$ alkyl substituted $NH_2$, $C_{3-10}$ branched or cycloalkyl substituted $NH_2$, $C_{1-10}$ dialkyl substituted $NH_2$, $C_{1-10}$ alkoxy, $C_{1-10}$ alkyl substituted thio, thiophenyl, halophenylthio, $C_{1-10}$ alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a $C_{3-10}$ ring.

In the foregoing chemical formula, the alkyl groups can be straight, branched, or cyclic, provided sufficient atoms are selected for the chemical formula. The $C_{1-30}$ substituted alkyl can include a wide variety of substituents, nonlimiting examples which include those selected from the group consisting of phenyl, pyridyl, furanyl, pyrrolidinyl, imidazonyl, $NH_2$, $C_{1-10}$ alkyl or dialkyl substituted $NH_2$, OH, SH, and $C_{1-10}$ alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

Pharmaceutically acceptable salts and derivatives of the bisphosphonates are also useful herein. Non-limiting examples of salts include those selected from the group consisting alkali metal, alkaline metal, ammonium, and mono-, di-, tri-, or tetra-$C_{1-30}$ alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated.

Nonlimiting examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof. A particularly preferred bisphosphonate is alendronate, especially a sodium, potassium, calcium, magnesium or ammonium salt of alendronic acid. Exemplifying the preferred bisphosphonate is a sodium salt of alendronic acid, especially a hydrated sodium salt of alendronic acid. The salt can be hydrated with a whole number of moles of water or non whole numbers of moles of water. Further exemplifying the preferred bisphosphonate is a hydrated sodium salt of alendronic acid, especially when the hydrated salt is alendronate monosodium trihydrate.

The precise dosage of the organic bisphosphonate will vary with the dosing schedule, the particular bisphosphonate chosen, the age, size, sex and condition of the mammal or human, the nature and severity of the disorder to be treated, and other relevant medical and physical factors. For humans, an effective oral dose of bisphosphonate is typically from about 1.5 to about 6000 μg/kg body weight and preferably about 10 to about 2000 μg/kg of body weight. In alternative dosing regimens, the bisphosphonate can be administered at intervals other than daily, for example once-weekly dosing, twice-weekly dosing, biweekly dosing, and twice-monthly dosing. In a once weekly dosing regimen, alendronate monosodium trihydrate would be administered at dosages of 35 mg/week or 70 mg/week. The bisphosphonates may also be administered monthly, ever six months, yearly or even less frequently, see WO 01/97788 (published Dec. 27, 2001) and WO 01/89494 (published Nov. 29, 2001).

"Estrogen" includes, but is not limited to naturally occurring estrogens [7-estradiol ($E_2$), estrone ($E_1$), and estriol ($E_3$)], synthetic conjugated estrogens, oral contraceptives and sulfated estrogens. See, Gruber C J, Tschugguel W, Schneeberger C, Huber J C., "Production and actions of estrogens" N Engl J Med 2002 Jan. 31; 346(5):340-52.

"Estrogen receptor modulators" refers to compounds which interfere or inhibit the binding of estrogen to the receptor, regardless of mechanism. Examples of estrogen receptor modulators include, but are not limited to, estrogen, progestogen, estradiol, droloxifene, raloxifene, lasofoxifene, TSE-424, tamoxifen, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Cathepsin K inhibitors" refers to compounds which interfere with the activity of the cysteine protease cathepsin K. Nonlimiting examples of cathepsin K inhibitors can be found in PCT publications WO 00/55126 to Axys Pharmaceuticals and WO 01/49288 to Merck Frosst Canada & Co. and Axys Pharmaceuticals.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases. See C. Farina et al., "Selective inhibitors of the osteoclast vacuolar proton ATPase as novel bone antiresorptive agents," DDT, 4: 163-172 (1999), which is hereby incorporated by reference in its entirety.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MBVACOR®; see U.S. Pat. Nos. 4,231,938, 4,294,926 and 4,319,039), simvastatin (ZOCOR® see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL® see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL® see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

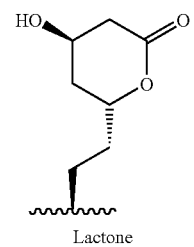

Lactone

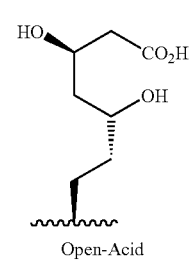

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically-acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl) aminomethane. Further examples of salt forms of HMG-CoA reductase inhibitors may include, but are not-limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

As used above, "integrin receptor antagonists" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. H. N. Lode and coworkers in PNAS USA 96: 1591-1596 (1999) have observed synergistic effects between an antiangiogenic αv integrin antagonist and a tumor-specific antibody-cytokine (interleukin-2) fusion protein in the eradication of spontaneous tumor metastases. Their results suggested this combination as having potential for the treatment of cancer and metastatic tumor growth. $\alpha_v\beta_3$ integrin receptor antagonists inhibit bone resorption through a new mechanism distinct from that of all currently available drugs. Integrins are heterodimeric transmembrane adhesion receptors that mediate cell-cell and cell-matrix interactions. The α and β integrin subunits interact non-covalently and bind extracellular matrix ligands in a divalent cation-dependent manner. The most abundant integrin on osteoclasts is $\alpha_v\beta_3$ (>$10^7$/osteoclast), which appears to play a rate-limiting role in cytoskeletal organization important for cell migration and polarization. The $\alpha_v\beta_3$ antagonizing effect is selected from inhibition of bone resorption, inhibition of restenosis, inhibition of macular degeneration, inhibition of arthritis, and inhibition of cancer and metastatic growth.

"An osteoblast anabolic agent" refers to agents that build bone, such as PTH. The intermittent administration of parathyroid hormone (PTH) or its amino-terminal fragments and analogues have been shown to prevent, arrest, partially reverse bone loss and stimulate bone formation in animals and humans. For a discussion refer to D. W. Dempster et al., "Anabolic actions of parathyroid hormone on bone," Endocr Rev 14: 690-709 (1993). Studies have demonstrated the clinical benefits of parathyroid hormone in stimulating bone formation and thereby increasing bone mass and strength. Results were reported by R M Neer et al., in New Eng J Med 344 1434-1441 (2001).

In addition, parathyroid hormone-related protein fragments or analogues, such as PTHrP-(1-36) have demonstrated potent anticalciuric effects [see M. A. Syed et al., "Parathyroid hormone-related protein-(1-36) stimulates renal tubular calcium reabsorption in normal human volunteers: implications for the pathogenesis of humoral hypercalcemia of malignancy," JCEM 86: 1525-1531 (2001)] and may also have potential as anabolic agents for treating osteoporosis.

Calcitonin is a 32 amino acid pepetide produced primarily by the thyroid which is known to participate in calcium and phosphorus metabolism. Calcitonin suppresses resorption of bone by inhibiting the activity of osteoclasts. Thus, calcitonin can allow osteoblasts to work more effectively and build bone.

"Vitamin D" includes, but is not limited to, vitamin $D_3$ (cholecalciferol) and vitamin $D_2$ (ergocalciferol), which are naturally occurring, biologically inactive precursors of the hydroxylated biologically active metabolites of vitamin D: 1α-hydroxy vitamin D; 25-hydroxy vitamin D, and 1α,25-dihydroxy vitamin D. Vitamin $D_2$ and vitamin $D_3$ have the same biological efficacy in humans. When either vitamin $D_2$ or $D_3$ enters the circulation, it is hydroxylated by cytochrome $P_{450}$-vitamin D-25-hydroxylase to give 25-hydroxy vitamin D. The 25-hydroxy vitamin D metabolite is biologically inert and is further hydroxylated in the kidney by cytochrome P450-monooxygenase, 25 (OH) D-1α-hydroxylase to give 1,25-dihydroxy vitamin D. When serum calcium decreases, there is an increase in the production of parathyroid hormone (PTH), which regulates calcium homeostasis and increases plasma calcium levels by increasing the conversion of 25-hydroxy vitamin D to 1,25-dihydroxy vitamin D.

1,25-dihydroxy vitamin D is thought to be reponsible for the effects of vitamin D on calcium and bone metabolism. The 1,25-dihydroxy metabolite is the active hormone required to maintain calcium absorption and skeletal integrity. Calcium homeostasis is maintained by 1,25 dihydroxy vitamin D by inducing monocytic stem cells to differentiate into osteoclasts and by maintaining calcium in the normal range, which results in bone mineralization by the deposition of calcium hydroxyapatite onto the bone surface, see Holick, M F, Vitamin D photobiology, metabolism, and clinical applications, In: DeGroot L, Besser H, Burger H G, eg al., eds. *Endocrinology*, $3^{rd}$ ed., 990-1013 (1995). However, elevated levels of 1α,25-dihydroxy vitamin $D_3$ can result in an increase of calcium concentration in the blood and in the abnormal control of calcium concentration by bone metabolism, resulting in hypercalcemia. 1α,25-dihydroxy vitamin $D_3$ also indirectly regulates osteoclastic activity in bone metabolism and elevated levels may be expected to increase excessive bone resorption in osteoporosis.

"Synthetic vitamin D analogues" includes non-naturally occurring compounds that act like vitamin D.

Selective Serotonin Reuptake Inhibitors act by increasing the amount of serotonin in the brain. SSRIs have been used successfully for a decade in the United States to treat depression. Non-limiting examples of SSRIs include fluoxetine, paroxetine, sertraline, citalopram, and fluvoxamine. SSRIs are also being used to treat disoreders realted to estrogen functioning, suchs as premenstrual syndrome and premenstrual dysmorphic disorder. See Sundstrom-Poromaa I, Bixo M, Bjorn I, Nordh O., "Compliance to antidepressant drug therapy for treatment of premenstrual syndrome," J Psychosom Obstet Gynaecol 2000 December; 21(4):205-11.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a bisphosphonate, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The present invention also encompasses a pharmaceutical composition useful in the treatment of osteoporosis or other bone disorders, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment. Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The compounds of the present invention can be used in combination with other agents useful for treating estrogen-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating cathepsin-mediated conditions includes in principle any combination with any pharmaceutical composition useful for treating disorders related to estrogen functioning.

The scope of the invention therefore encompasses the use of the instantly claimed compounds in combination with a second agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; a selective serotonin reuptake inhibitor; and the pharmaceutically acceptable salts and mixtures thereof.

These and other aspects of the invention will be apparent from the teachings contained herein.

Definitions

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating" or "treatment" of a disease as used herein includes: preventing the disease, i.e. causing the clinical symptoms of the disease not to develop in a mammal that may be exposed to or predisposed to the disease but does not yet experience or display symptoms of the disease; inhibiting the disease, i.e., arresting or reducing the development of the disease or its clinical symptoms; or relieving the disease, i.e., causing regression of the disease or its clinical symptoms.

The term "bone resorption," as used herein, refers to the process by which osteoclasts degrade bone.

The term "alkyl" shall mean a substituting univalent group derived by conceptual removal of one hydrogen atom from a straight or branched-chain acyclic saturated hydrocarbon (i.e., —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, etc.).

The term "alkenyl" shall mean a substituting univalent group derived by conceptual removal of one hydrogen atom from a straight or branched-chain acyclic unsaturated hydrocarbon containing at least one double bond (i.e., —CH=$CH_2$, —$CH_2$CH=$CH_2$, —CH=$CHCH_3$, —$CH_2$CH=$C(CH_3)_2$, etc.).

The term "alkynyl" shall mean a substituting univalent group derived by conceptual removal of one hydrogen atom from a straight or branched-chain acyclic unsaturated hydrocarbon containing at least one triple bond (i.e., —C≡CH, —$CH_2$C≡CH, —C≡$CCH_3$, —$CH_2$C≡$CCH_2(CH_3)_2$, etc.).

The term "alkylene" shall mean a substituting bivalent group derived from a straight or branched-chain acyclic saturated hydrocarbon by conceptual removal of two hydrogen atoms from different carbon atoms (i.e., —$CH_2CH_2$—, —$CH_2CH_2CH_2CH_2$—, —$CH_2C(CH_3)_2CH_2$—, etc.).

The term "alkylidene" shall mean a substituting bivalent group derived from a straight or branched-chain acyclic saturated hydrocarbon by conceptual removal of two hydrogen atoms from the same carbon atom (i.e., =$CH_2$, =$CHCH_3$, =$C(CH_3)_2$, etc.).

The term "alkenylene" shall mean a substituting bivalent group derived from a straight or branched-chain acyclic unsaturated hydrocarbon by conceptual removal of two hydrogen atoms from different carbon atoms (i.e., —CH=CH—, —$CH_2$CH=CH—, $CH_2$CH=$CHCH_2$—, —$C(CH_3)$=$C(CH_3)$—, etc.).

The term "cycloalkyl" shall mean a substituting univalent group derived by conceptual removal of one hydrogen atom from a saturated monocyclic hydrocarbon (i.e., cyclopropyl, cyclobutyl, cyclopentyl, cyclohexyl, or cycloheptyl).

The term "cycloalkenyl" shall mean a substituting univalent group derived by conceptual removal of one hydrogen atom from an unsaturated monocyclic hydrocarbon containing a double bond (i.e., cyclopentenyl or cyclohexenyl).

The term "heterocycloalkyl" shall mean a substituting univalent group derived by conceptual removal of one hydrogen atom from a heterocycloalkane wherein said heterocycloalkane is derived from the corresponding saturated monocyclic hydrocarbon by replacing one or two carbon atoms with atoms selected from N, O or S. Examples of heterocycloalkyl groups include, but are not limited to, oxiranyl, azetidinyl, pyrrolidinyl, piperidinyl, piperazinyl, and morpholinyl. Heterocycloalkyl substituents can be attached at a carbon atom. If the substituent is a nitrogen containing heterocycloalkyl substituent, it can be attached at the nitrogen atom.

The term "aryl" as used herein refers to a substituting univalent group derived by conceptual removal of one hydrogen atom from a monocyclic or bicyclic aromatic hydrocarbon. Examples of aryl groups are phenyl, indenyl, and naphthyl.

The term "heteroaryl" as used herein refers to a substituting univalent group derived by the conceptual removal of one hydrogen atom from a monocyclic or bicyclic aromatic ring system containing 1, 2, 3, or 4 heteroatoms selected from N, O, or S. Examples of heteroaryl groups include, but are not limited to, pyrrolyl, furyl, thienyl, imidazolyl, pyrazolyl, oxazolyl, isoxazolyl, thiazolyl, pyridyl, pyrimidinyl, pyrazinyl, benzimidazolyl, indolyl, and purinyl. Heteraryl substituents can be attached at a carbon atom or through the heteroatom.

In the compounds of the present invention, alkyl, alkenyl, alkynyl, alkylidene, alkenylene, cycloalkyl, cycloalkenyl, heterocycloalkyl, aryl and heteroaryl groups can be further substituted by replacing one or more hydrogen atoms by alternative non-hydrogen groups. These include, but are not limited to, halo, hydroxy, mercapto, amino, carboxy, cyano, carbamoyl, and oxo.

Whenever the term "alkyl" or "aryl" or either of their prefix roots appear in a name of a substituent (e.g., aryl $C_{1-8}$ alkyl) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, and chlorophenylethyl. Examples of alkylaryl include, but are not limited to, toluyl, ethylphenyl, and propylphenyl.

The term "(heteroaryl)alkyl," as used herein, shall refer to a system that includes a heteroaryl portion, where heteroaryl is as defined above, and contains an alkyl portion. Examples of (heteroaryl)alkyl include, but are not limited to, thienylmethyl, thienylethyl, thienylpropyl, pyridylmethyl, pyridylethyl and imidazoylmethyl.

The term "(cycloalkyl)alkyl," as used herein, shall refer to a system that includes a 3- to 7-membered fully saturated cyclic ring portion and also includes an alkyl portion, wherein cycloalkyl and alkyl are as defined above.

The term "(cycloalkyl)alkenyl," as used herein, shall refer to a system that includes a 3- to 7-membered fully saturated cyclic ring portion and also includes an alkenyl portion, wherein cycloalkyl and alkenyl are as defined above.

The term "(cycloalkenyl)alkyl," as used herein, shall refer to a system that includes a 3- to 7-membered cyclic ring portion containing at least one carbon to carbon double bond and also includes an alkyl portion, wherein cycloalkenyl and alkyl are as defined above.

The term "(heterocycloalkyl)alkyl," as used herein, shall refer to a system that includes a 3- to 7-membered heterocycloalkyl ring portion and also includes an alkyl portion, wherein heterocycloalkyl and alkyl are as defined above.

In the compounds of the present invention, $R^1$ and $R^2$ can be taken together with the carbon atom to which they are attached to form a 3-6 membered ring.

In the compounds of the present invention, $R^a$ and $R^b$ can be taken together with any of the atoms to which they may be attached or are between them to form a 4-6 membered ring system.

The term "halo" shall include iodo, bromo, chloro and fluoro.

The term "oxy" means an oxygen (O) atom. The term "thio" means a sulfur (S) atom. The term "oxo" means =O. The term "oximino" means the =N—O group.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. Also when compounds of Formula I contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, John Wiley & Sons, Inc. 1981, the disclosure of which is incorporated herein by reference in its entirety. The protected derivatives of compounds of Formula I can be prepared by methods well known in the art.

The alkyl, alkenyl, alkynyl, cycloalkyl, cycloalkenyl, aryl, heterocycloalkyl and heteroaryl substituents may be unsubstituted or unsubstituted, unless specifically defined otherwise. For example, a $C_{1-10}$alkyl may be substituted with one or more substituents selected from hydroxy, oxo, halogen, alkoxy, dialkylamino, or carboxy, and so on. In the case of a disubstituted alkyl, for instance, wherein the substituents are oxo and OH, the following are included in the definition: —(C=O)CH$_2$CH(OH)CH$_3$, —(C=O)OH, —CH$_2$(OH) CH$_2$CH(O), and so on. In the case of substituted alkyl, for instance, where the substituents are 1-5 fluoro, the following are included in the definition: —CHF$_2$, —CF$_3$, —CF$_2$CH$_3$, —CH$_2$CF$_3$, —CF$_2$CF$_3$, —CH$_2$CF$_2$CH$_3$, —CH$_2$CH$_2$CF$_3$, —CH$_2$CF$_2$CF$_3$, —CH$_2$CF$_2$CH$_2$CH$_3$, —CH$_2$CH$_2$CF$_2$CH$_3$, —CH$_2$CH$_2$CF$_2$CF$_3$, —CH$_2$CF(CH$_3$)$_2$, and so on. In the case of a cycloalkylalkyl group, for instance, wherein the substituents are 1-3 $C_{1-3}$allyl, the following are included in the definition:

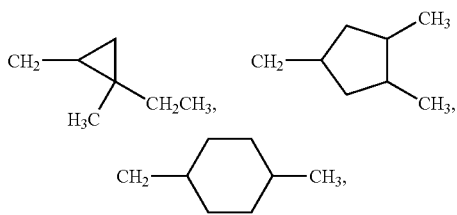

The compounds of the present invention may have asymmetric centers, chiral axes, and chiral planes (as described in: E. L. Eliel and S. H. Wilen, *Stereo-chemistry of Carbon Compounds*, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

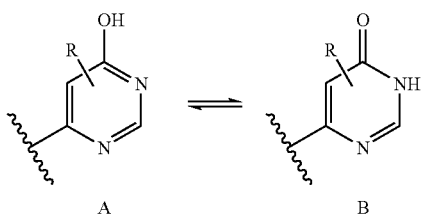

When any variable (e.g. $R^a$, $R^b$, $R^c$ etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

Under standard nonmenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

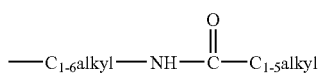

In choosing compounds of the present invention, one of ordinary skill in the art will recognize that the various substituents, i.e. $R^1, R^2, R^3, R^4, R^5, R^6, R^7, R^8, R^9, R^{10}, R^{11}, R^{12}, R^a, R^b, R^c, R^d, X, Y$ and $Z$ are to be chosen in conformity with well-known principles of chemical structure connectivity.

Representative compounds of the present invention typically display submicromolar affinity for alpha and/or beta estrogen receptors, and preferably agonize the beta estrogen receptor. Compounds of this invention are therefore useful in treating mammals suffering from disorders related to estrogen functioning.

The compounds of the present invention are available in racemic form or as individual enantiomers. For convenience, some structures are graphically represented as a single enantiomer but, unless otherwise indicated, is meant to include both racemic and enantiomerically pure forms. Where cis and trans sterochemistry is indicated for a compound of the present invention, it should be noted that the stereochemistry should be construed as relative, unless indicated otherwise. For example, a (+) or (−) designation should be construed to represent the indicated compound with the absolute stereochemistry as shown.

Racemic mixtures can be separated into their individual enantiomers by any of a number of conventional methods. These include, but are not limited to, chiral chromatography, derivatization with a chiral auxiliary followed by separation by chromatography or crystallization, and fractional crystallization of diastereomeric salts. Deracemization procedures may also be employed, such as enantiomeric protonation of a pro-chiral intermediate anion, and the like.

The compounds of the present invention can be used in combination with other agents useful for treating estrogen-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating estrogen-mediated conditions includes in principle any combination with any pharmaceutical composition useful for treating disorders related to estrogen functioning.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic and the like. The preparation of the pharmaceutically acceptable salts described above and other typical pharmaceutically acceptable salts is more fully described by Berg et al., "Pharmaceutical Salts," *J. Pharm. Sci.,* 1977:66:1-19, hereby incorporated by reference. The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The novel compounds of the present invention can be prepared according to the following schemes, using appropriate materials, and are exemplified by the subsequent specific examples. The compounds illustrated in the examples are not, however, to be construed as forming the only genus that is considered as the invention. Those skilled in the art will readily understand that known variations of the conditions and processes of the following preparative procedures can be used to prepare these compounds. All temperatures are degrees Celsius unless otherwise noted.

EXAMPLE 1

Synthesis of 3-Bromo-8a-Butyl-6-Hydroxy-8,8a-Dihydrocyclopenta[a]Inden-2(1H)-One

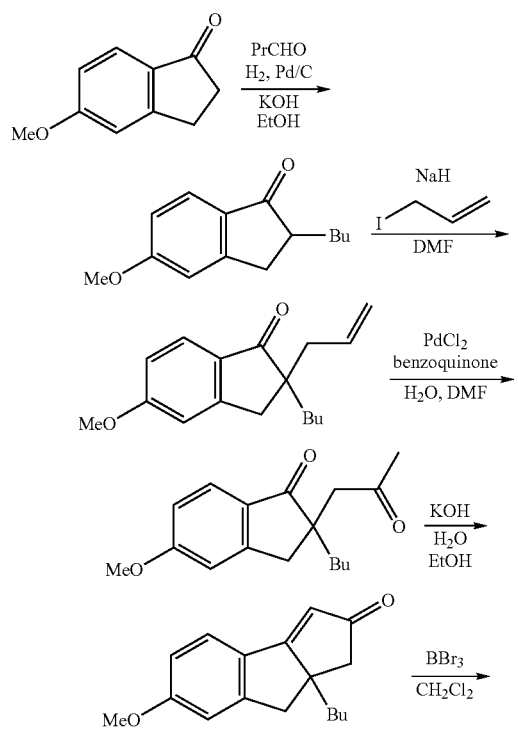

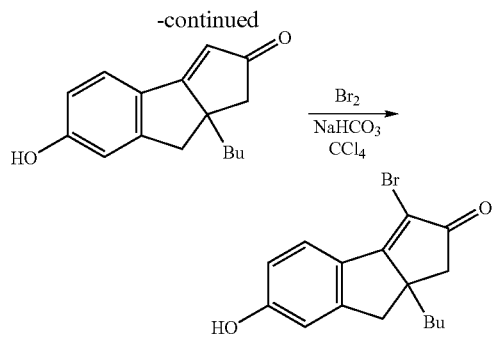

Step 1: 2-butyl-5-methoxy-1-indanone

Potassium hydroxide (0.44 g, 85% weight pure, 6.67 mmol) and 10% palladium on activated carbon (0.42 g) were added to a mixture of 5-methoxy-1-indanone (5.0 g, 30.8 mmol) and butyraldehyde (3.3 mL, 37 mmol) in ethanol (30 mL). The resulting mixture was stirred under an atmosphere of hydrogen at room temperature for 2 hours. The mixture was filtered and the filtrate evaporated under vacuum. The residue was partitioned between EtOAc (200 mL) and water (200 mL) containing 2N HCl (5 mL). The organic phase was washed with brine (100 mL), dried over $MgSO_4$, filtered, and evaporated under vacuum to afford crude 2-butyl-5-methoxy-1-indanone as an oil.

Step 2: 2-allyl-2-butyl-5-methoxy-1-indanone

A solution of 2-butyl-5-methoxy-1-indanone (500 mg, 2.3 mmol) in anhydrous N,N-dimethylformamide (DMF, 5 mL) was added to a suspension of sodium hydride (100 mg of a 60% dispersion in mineral oil, 2.5 mmol) in DMF (5 mL). The mixture was diluted with more DMF (2 mL, used to rinse in the indanone solution), placed under a nitrogen atmosphere, and stirred at room temperature for 25 minutes. Allyl iodide (0.32 mL, 3.5 mmol) was then added over 5 minutes, during which time the mixture clarified. After stirring at room temperature for an additional 15.5 hours, the mixture was partitioned between EtOAc (200 mL) and water (150 mL) containing brine. The aqueous phase was extracted with EtOAc (2×100 mL). The combined EtOAc solution was washed with brine, dried over $MgSO_4$, filtered, and concentrated under vacuum to afford an oil. The crude product was purified by Biotage™ (Charlottesville, Va.) flash chromatography on a 40S (4.0×7.0 cm) silica gel column, eluting with 49:1 hexanes-EtOAc. The product-containing fractions were evaporated under vacuum to afford 2-allyl-2-butyl-5-methoxy-1-indanone as an oil.

Step 3: 2-butyl-5-methoxy-(2-oxopropyl)-1-indanone

A solution of 2-allyl-2-butyl-5-methoxy-1-indanone (253 mg, 0.98 mmol) in DMF (1.2 mL) was treated with benzoquinone (108 mg, 0.98 mmol), water (0.026 mL, 1.44 mmol), and palladium(II) chloride (36 mg, 0.2 mmol). The mixture was stirred and heated in an oil bath at 65° C. Additional water was added in 0.026 mL portions after 15, 45, and 130 minutes. After 230 minutes, the mixture was treated with more benzoquinone (10.9 mg, 0.1 mmol) and, after 285 minutes, with more water (0.026 mL). After heating at 65° C. for a total of 345 minutes, the mixture was diluted with water (50 ml) and extracted with $Et_2O$ (40 mL) followed by $CH_2Cl_2$ (2×50 mL). The organic extracts were washed with brine, dried over $MgSO_4$, filtered, and concentrated under vacuum. The residue was purified by Biotage™ (Charlottesville, Va.) flash chromatography on a 12M (12 mm×15 cm) silica gel column, eluting with 10:1 hexane-EtOAc. The product-containing fractions were evaporated under vacuum to afford 2-butyl-5-methoxy-(2-oxopropyl)-1-indanone as an oil.

Step 4: 8a-butyl-6-methoxy-8,8a-dihydrocyclopenta[a]inden-2(1H)-one

Potassium hydroxide (8 g, 87% weight pure, 0.12 mol) was dissolved in 7:1 water-EtOH (80 mL) to give a 1.56M solution. A suspension of 2-butyl-5-methoxy-(2-oxopropyl)-1-indanone (83 mg, 0.3 mmol) in 5 mL of the KOH solution was stirred and heated at reflux for 23 hours. After cooling, the mixture was diluted with water (10 mL) and extracted with EtOAc (3×30 mL). The extracts were washed with 1N HCl, water, and brine (20 mL each), dried over $MgSO_4$, filtered, and concentrated under vacuum to an oil. $^1H$ NMR revealed a 65:35 mixture of desired product to starting material. The mixture was purified by preparative layer chromatography on a 0.1×20×20 cm silica gel GF plate (Analtech, Newark, Del.), developing twice with 5:1 hexane-EtOAc. The product band was extracted with EtOAc and the extracts evaporated under vacuum to provide 8a-butyl-6-methoxy-8,8a-dihydrocyclopenta[a]inden-2(1H)-one as an oil.

Step 5: 8a-butyl-6-hydroxy-8,8a-dihydrocyclopenta[a]inden-2(1H)-one

A solution of 8a-butyl-6-methoxy-8,8a-dihydrocyclopenta[a]inden-2(1H)-one (37 mg, 0.14 mmol) in anhydrous $CH_2Cl_2$ (1.4 mL) was placed under a nitrogen atmosphere, cooled in a dry ice-acetone bath, and treated over two minutes with 1M $BBr_3$ in $CH_2Cl_2$ (0.42 mL, 0.42 mmol). The cooling bath was removed and the reaction mixture was stirred at room temperature for 3 hours. Additional 1M $BBr_3$ in $CH_2Cl_2$ (0.1 mL, 0.1 mmol) was added and the mixture was stirred at room temperature overnight. The mixture was partitioned between EtOAc and aqueous 1N HCl. The organic phase was washed with 5% $NaHCO_3$ and brine, dried over $MgSO_4$, filtered, and evaporated under vacuum to provide a solid residue. Recrystallization of this material from hot EtOAc gave pure 8a-butyl-6-hydroxy-8,8a-dihydrocyclopenta[a]inden-2(1H)-one (11 mg). Concentration of the mother liquors gave additional product contaminated with ~5% of starting material.

$^1H$ NMR ($CDCl_3$, 500 MHz) δ 0.81 (t, $CH_2CH_2CH_2CH_3$), 1.11-1.23 (m, $CH_2CH_2CH_2CH_3$), 1.38 and 1.61 (two m, $CH_2CH_2CH_2CH_3$), 2.52 and 2.56 (two d, 1-$CH_2$), 2.86 and 2.97 (two d, 8-$CH_2$), 5.52 (s, OH), 6.00 (s, H-3), 6.79 (dd, H-5), 6.82 (d, H-7), and 7.48 (d, H-4); mass spectrum m/z 243.1 (M+1).

Step 6: 3-bromo-8a-butyl-6-hydroxy-8,8a-dihydrocyclopenta[a]inden-2(1H)-one

Bromine (0.005 mL, 0.095 mmol) was added to an ice-cold mixture of 8a-butyl-6-hydroxy-8,8a-dihydrocyclopenta[a]inden-2(1H)-one (23 mg, 0.095 mmol) and $NaHCO_3$ (40 mg, 0.48 mmol) in $CCl_4$ (0.3 mL). The resulting mixture was stirred at 0-5° C. for 45 minutes, then diluted with $CH_2Cl_2$ (30 mL) and washed with water (30 mL). The aqueous phase was back-extracted with $CH_2Cl_2$ (2×10 mL). The combined organics were washed with saturated aqueous $Na_2S_2O_3$, dried over $MgSO_4$, filtered, and evaporated under vacuum to provide an off-white solid. Recrystallization from hexane/$CH_2Cl_2$ afforded 3-bromo-8a-butyl-6-hydroxy-8,8a-dihydrocyclopenta[a]inden-2(1H)-one as small, white needles.

$^1H$ NMR ($CDCl_3$, 500 MHz) δ 0.81 (t, $CH_2CH_2CH_2CH_3$), 1.10-1.24 (m, $CH_2CH_2CH_2CH_3$), 1.45 and 1.64 (two m, $CH_2CH_2CH_2CH_3$), 2.62 and 2.71 (two d, 1-$CH_2$), 2.90 and 3.01 (two d, 8-$CH_2$), 5.23 (d, OH), 6.84 (br s, H-7), 6.85 (dd, H-5), and 7.86 (d, H-4).

EXAMPLE 2

Synthesis of (RAC)-(1S,8aR)-3-Bromo-8a-Butyl-6-Hydroxy-1-Propyl-8,8a-Dihydrocyclopenta[a]Inden-2(1H)-One

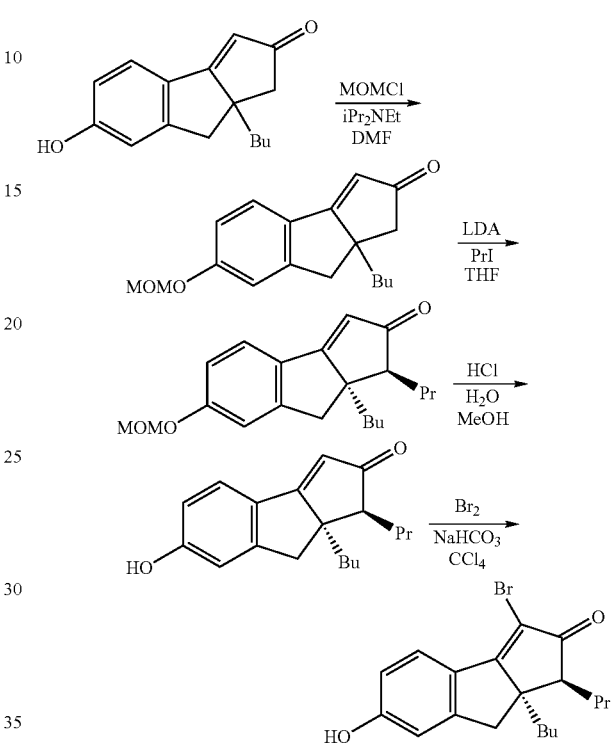

Step 1: 8a-butyl-6-(methoxymethoxy)-8,8a-dihydrocyclopenta[a]inden-2(1H)-one

A solution of 8a-butyl-6-hydroxy-8,8a-dihydrocyclopenta[a]inden-2(1H)-one (300 mg, 1.2 mmol) in anhydrous DMF (3 mL) was placed under a $N_2$ atmosphere and stirred at room temperature while N,N-diisopropylethylamine (0.63=L, 3.6 mmol) and chloromethyl methyl ether (0.183 mL, 2.4 mmol) were added successively. After stirring at room temperature overnight, the mixture was diluted with EtOAc (100 mL) and washed with 1N HCl. The acid wash was back-extracted with EtOAc. The combined organics were washed with 5% $NaHCO_3$, water and brine, dried over $MgSO_4$, filtered, and concentrated under vacuum to a brown oil. The crude product was purified by Biotage™ (Charlottesville, Va.) flash chromatography on a 40S (4×7 cm) silica gel column, eluting with 5:1 hexane-EtOAc, to provide 8a-butyl-6-(methoxymethoxy)-8,8a-dihydrocyclopenta[a]inden-2(1H)-one as an oil.

Step 2: (rac)-(1S,8aR)-8a-butyl-6-(methoxyethoxy)-1-propyl-8,8a-dihydrocyclpenta[a]inden-2(1H)-one A solution of 8a-butyl-6-(methoxymethoxy)-8,8a-dihydrocyclopenta[a]inden-2(1H)-one (109 mg, 0.38 mmol) in anhydrous tetrahydrofuran (THF, 2 mL) was placed under a $N_2$ atmosphere and cooled in an ice bath. Freshly prepared lithium diisopropylamide in THF (1.2 mL of a 0.4M solution, 0.48 mmol) was added and the resulting solution was stirred at 0-5° C. for 25 minutes. Propyl iodide (0.185 in L, 1.9 mmol) was then added and the mixture was stirred overnight with gradual warming to room temperature. The mixture was diluted with EtOAc, washed with 1N HCl, 5% $NaHCO_3$, and brine, dried over MgSO₄, filtered, and evaporated under vacuum. The residue (125 mg) was purified by Biotage™ (Charlottesville, Va.) flash chromatography on a 12S (1.2×7.5 cm) silica gel column, eluting with 19:1 hexane-EtOAc, to afford (rac)-(1S,8aR)-8a-butyl-6-(methoxymethoxy)-1-propyl-8,8a-dihydrocyclopenta[a]inden-2(1H)-one as an oil.

Step 3: (rac)-(1S,8aR)-8a-butyl-6-hydroxy-1-propyl-8,8a-dihydrocyclopenta[a]inden-2(1H)-one A solution of (rac)-(1S,8aR)-8a-butyl-6-(methoxymethoxy)-1-propyl-8,8a-dihydrocyclopenta[a]inden-2(1H)-one (92 mg, 0.28 mmol) in methanol (1 mL) was treated with aqueous 2N HCl (0.42 mL, 0.84 mmol). The resulting mixture was stirred and gradually heated to 80° C. over 30 minutes, and then kept at 80° C. for an additional 30 minutes. After cooling, the mixture was diluted with EtOAc and washed with 5% NaHCO₃. The aqueous portion was back-extracted with EtOAc. The combined organics were washed with brine, dried over MgSO₄, filtered, and concentrated under vacuum. The residue was purified by Biotage™ (Charlottesville, Va.) flash chromatography on a 12S (1.2×7.5 cm) silica gel column, eluting with 5:1 hexane-EtOAc, to give (rac)-(1S,8aR)-8a-butyl-6-hydroxy-1-propyl-8,8a-dihydrocyclopenta[a]inden-2(1H)-one as a white solid.

Step 4: (rac)-(1S,8aR)-3-bromo-8a-butyl-6-hydroxy-1-propyl-8,8a-dihydrocyclopenta[a]inden-2(1H)-one Bromine (0.0072 mL, 0.14 mmol) was added to an ice-cold mixture of (rac)-(1S,8aR)-8a-butyl-6-hydroxy-1-propyl-8,8a-dihydrocyclopenta[a]inden-2(1H)-one (40 mg, 0.14 mmol) and NaHCO₃ (59 mg, 0.70 mmol) in CCl₄ (0.48 mL). The resulting mixture was sonicated for 20 seconds and then stirred at 0-5° C. for 70 minutes. The mixture was diluted with CH₂Cl₂ (30 mL) and washed with water (30 mL), and the aqueous phase was back-extracted with CH₂Cl₂ (2×10 mL). The combined organics were washed with saturated aqueous Na₂S₂O₃, dried over MgSO₄, filtered, and evaporated under vacuum. The residue was purified by Biotage™ (Charlottesville, Va.) flash chromatography on a 12S (1.2×7.5 cm) silica gel column, eluting with 10:1 hexane-EtOAc, to give a clear oil. This material was further purified by preparative layer chromatography on a 0.1×20×20 cm silica gel GF plate (Analtech, Newark, Del.), developing twice with 5:1 hexane-EtOAc. The major UV visible band provided (rac)-(1S,8aR)-3-bromo-8a-butyl-6-hydroxy-1-propyl-8,8a-dihydrocyclopenta[a]inden-2(1H)-one as an oil.

$^1$H NMR (CDCl₃, 500 MHz) δ 0.80 (t, CH₂CH₂CH₂CH₃), 0.91 (t, CH₂CH₂CH₃), 1.07-1.22, 1.33-1.49, and 1.54-1.65 (three m, CH₂CH₂CH₃ and CH₂CH₂CH₂CH₃), 2.59 (dd, 1-CH₂), 2.80 and 2.98 (two d, 8-CH₂), 6.93 (m, H-5 and H-7), 7.10 (br s, OH), and 7.89 (d, H-4); mass spectrum m/z 363.1 (M+1) and 365.1 (M+3).

EXAMPLE 3

Synthesis of 1,3a-Diethyl-7-Hydroxy-3,3a,4,5-Tetrahydro-2H-Cyclopenta[a]Naphthalen-2-One

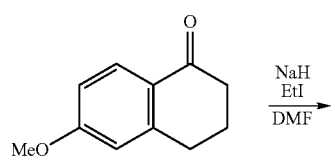

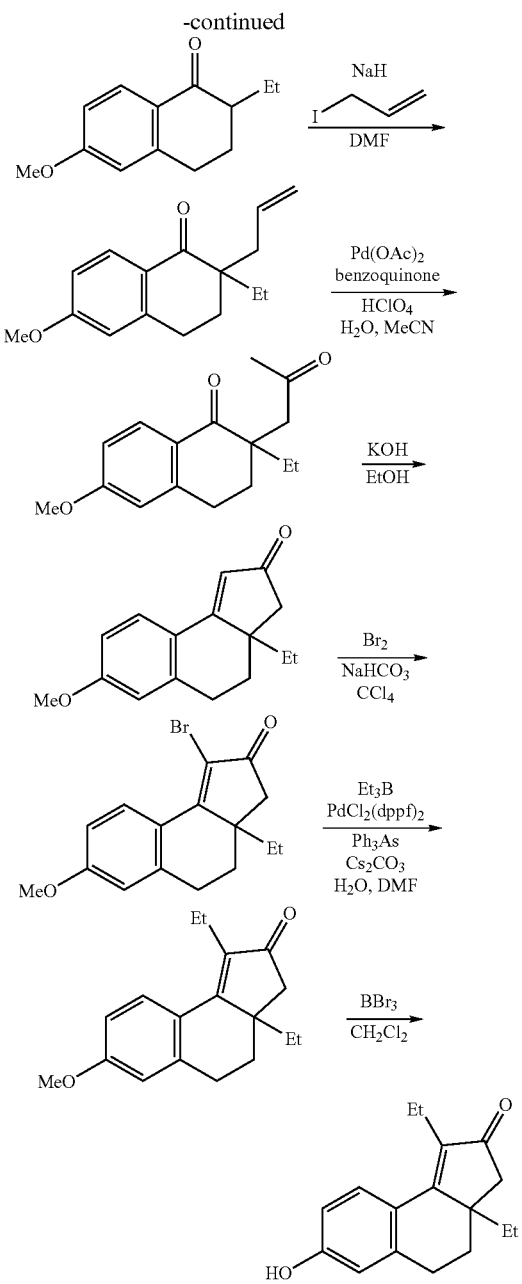

Step 1: 2-ethyl-6-methoxy-3,4-dihydro-1(2H)-naphthalenone

A solution of 6-methoxy-3,4-dihydro-1(2H)-naphthalenone (5.0 g, 28 mmol) in anhydrous N,N-dimethylformamide (DMF, 60 mL) was purged with N₂, cooled in an ice bath, stirred, and treated with NaH (1.2 g of a 60% dispersion in mineral oil, 30 mmol). The cooling bath was removed and the mixture was stirred at room temperature for 10 minutes. The mixture was re-cooled in an ice bath, treated with iodoethane (3.35 mL, 42 mmol), and then stirred under a N₂ atmosphere while gradually warming to room temperature. After stirring for 2.9 days, the mixture was diluted with EtOAc (250 mL) and washed with water (200 mL), and the aqueous phase was back-extracted with EtOAc (100 mL). The combined organics were washed with brine, dried over MgSO₄, filtered, and concentrated under vacuum. The residue was purified by Biotage™ (Charlottesville, Va.) flash chromatography on a 40M (4×15 cm) silica gel column, eluting successively with 1000 mL portions of 0.2%, 1%, 2%, and 5% EtOAc in hexane. The product-containing fractions were combined and evaporated under vacuum to afford 2-ethyl-6-methoxy-3,4-dihydro-1(2H)-naphthalenone as an oil.

Step 2: 2-allyl-2-ethyl-6-methoxy-3,4-dihydro-1(2H)-naphthalenone

NaH (0.31 g of a 60% dispersion in mineral oil, 7.6 mmol) was added to an ice-cold solution of 2-ethyl-6-methoxy-3,4-dihydro-1(2H)-naphthalenone (1.48 g, 7.2 mmol) in anhydrous DMF (14.4 mL). The mixture was purged with $N_2$ and stirred at 0-5° C. for 45 minutes. Allyl iodide (1.0 mL, 10.9 mmol) was added and, after a few minutes, the cooling bath was removed. After stirring overnight at room temperature, the mixture was partitioned between EtOAc and water, and the aqueous phase was back-extracted several times with EtOAc. The combined organics were washed with brine, dried over $MgSO_4$, filtered, and concentrated under vacuum. The residue was purified by Biotage™ (Charlottesville, Va.) flash chromatography to afford 2-allyl-2-ethyl-6-methoxy-3,4-dihydro-1(2H)-naphthalenone as an oil.

Step 3: 2-ethyl-6-methoxy-2-(2-oxopropyl)-3,4-dihydro-1(2H)-naphthalenone

A solution of 2-allyl-2-ethyl-6-methoxy-3,4-dihydro-1(2H)-naphthalenone (931 mg, 3.82 mmol) in acetonitrile (11 mL) was treated with benzoquinone (619 mg, 5.73 mmol), palladium(II) acetate (172 mg, 0.76 mmol), water (0.56 mL, 31 mmol), and perchloric acid (70%, 0.15 mL, 1.74 mmol). The resulting mixture was stirred overnight at room temperature, then filtered through a small plug of silica gel. The filtrate was diluted with $CH_2Cl_2$, washed with water, and the aqueous phase was back-extracted with $CH_2Cl_2$. The combined organics were washed with brine, dried over $MgSO_4$, filtered, and concentrated under vacuum to afford crude 2-ethyl-6-methoxy-2-(2-oxopropyl)-3,4-dihydro-1(2H)-naphthalenone as an orange oil.

Step 4: 3a-ethyl-7-methoxy-3,3a,4,5-tetrahydro-2H-cyclopenta[a]naphthalen-2-one

A solution of crude 2-ethyl-6-methoxy-2-(2-oxopropyl)-3,4-dihydro-1(2H)-naphthalenone (758 mg, 3 mmol) in EtOH (15 mL) was treated with freshly prepared 2N KOH in EtOH (1.5 mL, 3 mmol). The resulting solution was heated at reflux for 24 hours. After cooling, the mixture was diluted with EtOAc (70 mL) and washed with 1N HCl (35 mL) followed by 5% $NaHCO_3$ (35 mL). The $NaHCO_3$ phase was back-extracted with EtOAc (60 mL). The combined organics were washed with water and brine, dried over $MgSO_4$, filtered, and concentrated under vacuum. The residue was purified by Biotage™ (Charlottesville, Va.) flash chromatography on a 40 M (4×15 cm) silica gel column, eluting with 4:1 hexane-EtOAc, to provide 3a-ethyl-7-methoxy-3,3a,4,5-tetrahydro-2H-cyclopenta[a]naphthalen-2-one as an oil.

Step 5: 1-bromo-3a-ethyl-7-methoxy-3,3a,4,5-tetrahydro-2H-cyclopenta[a]naphthalen-2-one A solution of 3a-ethyl-7-methoxy-3,3a,4,5-tetrahydro-2H-cyclopenta[a]naphthalen-2-one (415 mg, 1.7 mol) in $CCl_4$ (5.1 mL) was treated with $NaHCO_3$ (714 mg, 8.5 mmol). The mixture was cooled in an ice bath, purged with $N_2$, stirred, and treated with $Br_2$ (0.088 mL, 1.7 mmol) to give an unstirrable orange gum. The mixture was sonicated for one minute, swirled in an ice bath for two minutes, and then stirred at 0-5° C. for 75 minutes. The mixture was then partitioned between $CH_2Cl_2$ and water (50 mL each). The organic phase was washed with saturated aqueous $Na_2S_2O_3$ and brine, dried over $MgSO_4$, filtered, and evaporated under vacuum. The crude product was purified by Biotage™ (Charlottesville, Va.) flash chromatography on a 40M (4×15 cm) silica gel column, eluting with 5:1 hexane-EtOAc, to provide 1-bromo-3a-ethyl-7-methoxy-3,3a,4,5-tetrahydro-2H-cyclopenta[a]naphthalen-2-one as a white foam.

Step 6: 1,3a-diethyl-7-methoxy-3,3a,4,5-tetrahydro-2H-cyclopenta[a]naphthalen-2-one A solution of 1-bromo-3a-ethyl-7-methoxy-3,3a,4,5-tetrahydro-2H-cyclopenta[a]naphthalen-2-one (120 mg, 0.37 mmol) in DMF (3 mL) was treated with [1,1'-bis(diphenylphosphino)ferrocene]dichloropalladium(II) dichloromethane complex (61 mg, 0.075 mmol), triphenylarsine (23 mg, 0.075 mmol), water (0.22 mL, 12.2 mmol), $Cs_2CO_3$ (244 mg, 0.75 mmol), and triethylborane (0.75 mL of a 1.0M solution in tetrahydrofuran, 0.75 mmol). The resulting mixture was placed under a $N_2$ atmosphere, stirred, and heated in an oil bath at 55-65° C. for 100 minutes. After cooling, the mixture was quenched with saturated aqueous $NH_4Cl$ and diluted with $CH_2Cl_2$. The organic phase was dried over $MgSO_4$ and filtered through a pad of silica gel, washing through with EtOAc. The filtrate was evaporated under vacuum to remove the solvents. The residue was purified by preparative layer chromatography on two 0.1×20×20 cm silica gel GF plates (Analtech, Newark, Del.), developing with 4:1 hexane-EtOAc. The UV visible product band was extracted with 5% MeOH in $CH_2Cl_2$ and the extracts evaporated under vacuum to provide 1,3a-diethyl-7-methoxy-3,3a,4,5-tetrahydro-2H-cyclopenta[a]naphthalen-2-one as a crystalline solid.

Step 7: 1,3a-diethyl-7-hydroxy-3,3a,4,5-tetrahydro-2H-cyclopenta[a]naphthalen-2-one A solution of 1,3a-diethyl-7-methoxy-3,3a,4,5-tetrahydro-2H-cyclopenta[α]naphthalen-2-one (10 mg, 0.036 mmol) in anhydrous $CH_2Cl_2$ (0.36 mL) was cooled in an ice bath, stirred under a $N_2$ atmosphere, and treated with 1M $BBr_3$ in $CH_2Cl_2$ (0.11 mL, 0.11 mmol). The resulting yellow suspension was stirred at 0-5° C. for 170 minutes and then treated with 1N HCl in diethyl ether (0.20 mL). The resulting mixture was purified by preparative layer chromatography on a 0.1× 20×20 cm silica gel GF plate (Analtech, Newark, Del.), developing with 1:1 hexane-EtOAc. The UV visible product band was eluted with 5% methanol in $CH_2Cl_2$ and the eluant was evaporated under vacuum to afford 1,3a-diethyl-7-hydroxy-3,3a,4,5-tetrahydro-2H-cyclopenta[a]naphthalen-2-one as a white solid.

$^1$H NMR (CDCl$_3$, 500 MHz) δ 0.76 (t, 3a-CH$_2$CH$_3$), 1.12 (t, 1-CH$_2$CH$_3$), 1.38 and 1.51 (two dq, 3a-CH$_2$CH$_3$), 1.75 and 2.16 (two ddd, 4-CH$_2$), 2.09 and 2.50 (two d, 3-CH$_2$), 2.39 and 2.52 (two dq, 1-CH$_2$CH$_3$), 2.86 and 2.99 (dd and ddd, 5-CH$_2$), 5.63 (d, OH), 6.71 (d, H-6), 6.78 (dd, H-8), and 7.51 (d, H-9); mass spectrum m/z 257.3 (M+1) and 320.3 (M+MeCN+Na).

EXAMPLE 4

Synthesis of 3a-Butyl-7-Hydroxy-3,3a,4,5-Tetrahydro-2H-Cyclopenta[a]Naphthalen-2-One

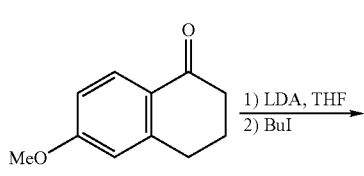

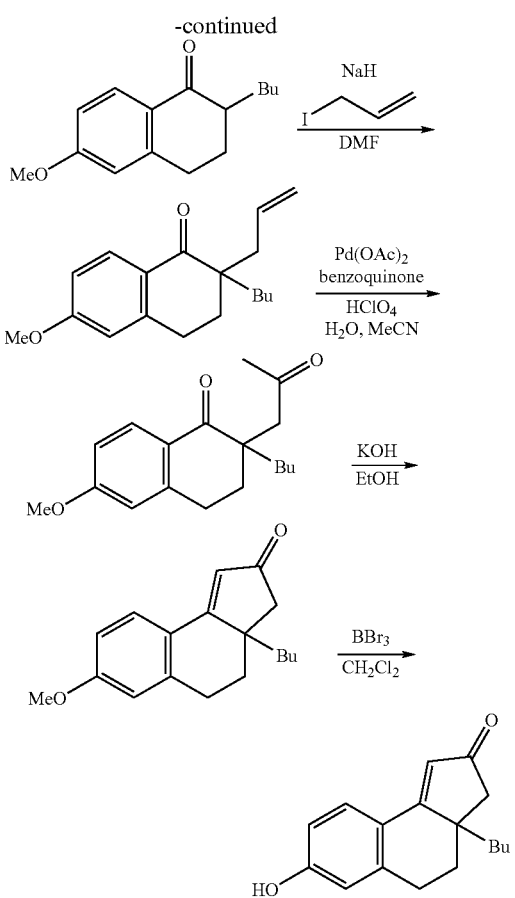

Step 1: 2-butyl-6-methoxy-3,4-dihydro-1(2H)-naphthalenone

A solution of 6-methoxy-3,4-dihydro-1(2H)-naphthalenone (5.29 g, 30 mmol) in anhydrous tetrahydrofuran (THF, 150 mL) was placed under a N₂ atmosphere, cooled in an ice bath, stirred, and treated with lithium diisopropylamide (90 mL of a 0.4M solution in THF, 36 mmol) dropwise over 13 minutes. The mixture was stirred at 0-5° C. for 30 minutes, then cooled in a dry ice-acetone bath to −78° C. and treated all at once with iodobutane (17.04 mL, 150 mmol). The resulting mixture was allowed to slowly warm to room temperature and stirred at room temperature overnight. The mixture was quenched with saturated aqueous NH₄Cl and concentrated under vacuum. The residue in EtOAc was washed with 5% NaHCO₃ and brine, dried over MgSO₄, filtered, and evaporated under vacuum. The crude product was purified by Biotage™ (Charlottesville, Va.) flash chromatography on a 40M (4×15 cm) silica gel column, eluting successively with 1000 mL portions of 0.1%, 0.2%, 1%, 2%, and 5% EtOAc in hexane. The product-containing fractions were evaporated under vacuum to afford 2-butyl-6-methoxy-3,4-dihydro-1(2H)-naphthalenone as an oil.

Step 2: 2-allyl-2-butyl-6-methoxy-3,4-dihydro-1(2H)-naphthalenone

NaH (0.32 g of a 60% dispersion in mineral oil, 8.0 mmol) was added to an ice-cold solution of 2-butyl-6-methoxy-3,4-dihydro-1(2H)-naphthalenone (1.55 g, 6.7 mmol) in anhydrous DMF (30 mL). The mixture was purged with N₂ and stirred at 0-5° C. for 45 minutes. Allyl iodide (0.91 mL, 10.0 mmol) was added and, after a few minutes, the cooling bath was removed and the mixture was stirred overnight at room temperature. Additional NaH (0.16 g of a 61.1% dispersion in mineral oil, 4.1 mmol) was added and the mixture was stirred at room temperature for 15 minutes. Allyl iodide (0.46 mL, 5.0 mmol) was added and the mixture was stirred at room temperature for 24 hours. The mixture was partitioned between EtOAc and water, and the aqueous phase was back-extracted with several portions of EtOAc. The combined organics were washed with brine, dried over MgSO₄, filtered, and concentrated under vacuum. The residue was purified by Biotage™ (Charlottesville, Va.) flash chromatography on a 40M (4×15 cm) silica gel column, eluting with 1% to 4% EtOAc in hexane, to afford 2-allyl-2-butyl-6-methoxy-3,4-dihydro-1(2H)-naphthalenone as an oil.

Step 3: 2-butyl-6-methoxy-2-(2-oxopropyl)-3,4-dihydro-1(2H)-naphthalenone

A solution of 2-allyl-2-butyl-6-methoxy-3,4-dihydro-1(2H)-naphthalenone (931 mg, 3.4 mmol) in acetonitrile (10 mL) was treated with benzoquinone (553 mg, 5.12 mmol), palladium(II) acetate (155 mg, 0.69 mmol), water (0.50 mL, 28 mmol), and perchloric acid (70%, ~0.14 mL, 1.6 mmol). The resulting mixture was stirred overnight at room temperature. The mixture was partitioned between CH₂Cl₂ (200 mL) and water (100 mL) and the aqueous phase was back-extracted with CH₂Cl₂ (2×75 mL). The combined organics were washed with brine, dried over MgSO₄, filtered, and concentrated under vacuum. The residue (1.17 g) was purified by Biotage™ (Charlottesville, Va.) flash chromatography on a 40S (4×7 cm) silica gel column, eluting with 10:1 to 5:1 hexane-EtOAc. The product-containing fractions were evaporated under vacuum to afford 2-butyl-6-methoxy-2-(2-oxopropyl)-3,4-dihydro-1(2H)-naphthalenone as an oil.

Step 4: 3a-butyl-7-methoxy-3,3a,4,5-tetrahydro-2H-cyclopenta[a]naphthalen-2-one

A solution of crude 2-butyl-6-methoxy-2-(2-oxopropyl)-3,4-dihydro-1(2H)-naphthalenone (888 mg, ~3 mmol) in EtOH (15 mL) was treated with freshly prepared 2N KOH in EtOH (1.5 mL, 3 mmol). The resulting solution was placed under a N₂ atmosphere and heated at reflux for 17 hours. After cooling, the mixture was diluted with water (100 mL) and extracted with EtOAc (3×100 mL). The extracts were washed with brine, dried over MgSO₄, filtered, and concentrated under vacuum. The residue was purified by Biotage™ (Charlottesville, Va.) flash chromatography on a 40S (4×7 cm) silica gel column, eluting with 1000 mL portions of 19:1 and 10:1 hexane-EtOAc. The product-containing fractions were evaporated under vacuum to provide 3a-butyl-7-methoxy-3,3a,4,5-tetrahydro-2H-cyclopenta[a]naphthalen-2-one as an oil.

Step 5: 3a-butyl-7-hydroxy-3,3a,4,5-tetrahydro-2H-cyclopenta[a]naphthalen-2-one

A solution of 3a-butyl-7-methoxy-3,3a,4,5-tetrahydro-2H-cyclopenta[α]naphthalen-2-one (598 mg, 2.2 mmol) in anhydrous CH₂Cl₂ (22 mL) was placed under a N₂ atmosphere, cooled in a dry ice-acetone bath (−78° C.), and stirred while 1M BBr₃ in CH₂Cl₂ (6.6 mL, 6.6 mmol) was added dropwise over 4 minutes. After stirring at −78° C. for 5 minutes, the cooling bath was removed and the mixture was stirred at room temperature for 160 minutes. Additional 1M BBr₃ in CH₂Cl₂ (1.4 mL) was added and the mixture was stirred at room temperature for 60 minutes. The mixture was diluted with EtOAc, washed with 1N HCl, 5% NaHCO₃, water, and brine, dried over MgSO₄, filtered, and evaporated under vacuum to give an orange-red solid. The crude product was purified by Biotage™ (Charlottesville, Va.) flash chromatography on a 40S (4×7 cm) silica gel column, eluting successively with 5:1, 2:1, and 1:1 hexane-EtOAc followed by EtOAc. The product-containing fractions were evaporated under vacuum to afford 3a-butyl-7-hydroxy-3,3a,4,5-tetrahydro-2H-cyclopenta[a]naphthalen-2-one as a solid.

$^1$H NMR (CDCl$_3$, 500 MHz) δ 0.80 (t, CH$_2$CH$_2$CH$_2$CH$_3$), 1.09, 1.14-1.29, and 1.55 (three m, CH$_2$CH$_2$CH$_2$CH$_3$), 1.75 and 2.11 (ddd and dd, 4-CH$_2$), 2.15 and 2.49 (two d, 3-CH$_2$), 2.75 and 2.93 (dd and ddd, 5-CH$_2$), 4.74 (br s, OH), 6.10 (s, H-1), 6.62 (d, H-6), 6.70 (dd, H-8), and 7.45 (d, H-9).

EXAMPLE 5

Synthesis of 1-Bromo-3a-Butyl-7-Hydroxy-3,3a,4,5-Tetrahydro-2H-Cyclopenta[a]Naphthalen-2-One and 1,6-Dibromo-3a-Butyl-7-Hydroxy-3,3a,4,5-Tetrahydro-2H-Cyclopenta[α]Naphthalen-2-One

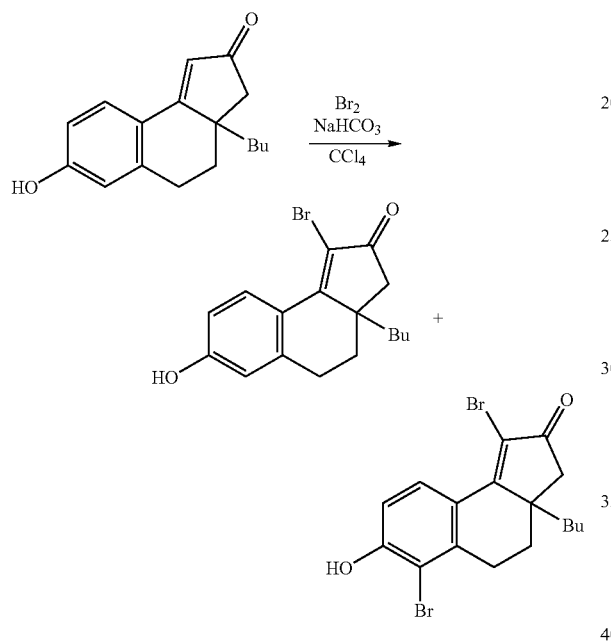

A suspension of 3a-butyl-7-hydroxy-3,3a,4,5-tetrahydro-2H-cyclopenta[a]naphthalen-2-one (408 mg, 1.59 mmol) in CCl$_4$ (5 mL) was treated with NaHCO$_3$ (667 mg, 7.95 mmol). The resulting mixture was placed under a N$_2$ atmosphere, cooled in an ice bath, and stirred while Br$_2$ (0.082 mL, 1.59 mmol) was added dropwise over one minute. The resulting dark red suspension was stirred at 0-5° C. for 55 minutes, then diluted with CH$_2$Cl$_2$ and washed with water followed by saturated Na$_2$S$_2$O$_3$. The organic phase was dried over MgSO$_4$, filtered, and evaporated under vacuum. The crude product was purified by Biotage™ (Charlottesville, Va.) flash chromatography on a 40S (4×7 cm) silica gel column, eluting with 4:1 hexane-EtOAc. Early fractions provided pure 1,6-dibromo-3a-butyl-7-hydroxy-3,3a,4,5-tetrahydro-2H-cyclopenta[a]naphthalen-2-one and later fractions provided impure 1-bromo-3a-butyl-7-hydroxy-3,3a,4,5-tetrahydro-2H-cyclopenta[a]naphthalen-2-one. A pure sample of the monobromo product was obtained by preparative layer chromatography on a 0.1×20×20 cm silica gel GF plate (Analtech, Newark, Del.), developing four times with 4:1 hexane-EtOAc.

$^1$H NMR (CDCl$_3$, 500 MHz) 1,6-dibromo product δ 0.82 (t, CH$_2$CH$_2$CH$_2$CH$_3$), 1.00-1.10 and 1.15-1.29 (two m, CH$_2$CH$_2$CH$_2$CH$_3$), 1.35 and 1.51 (two m, CH$_2$CH$_2$CH$_2$CH$_3$), 1.85 and 2.27 (ddd and dd, 4-CH$_2$), 2.28 and 2.68 (two d, 3-CH$_2$), 2.83 and 3.01 (ddd and dd, 5-CH$_2$), 6.14 (s, OH), 7.07 (d, H-8), and 8.40 (d, H-9); mass spectrum m/z 413.0 (M+1), 415.0, and 417.0.

$^1$H NMR (CDCl$_3$, 500 MHz) 1-bromo product δ 0.79 (t, CH$_2$CH$_2$CH$_2$CH$_3$), 1.00-1.09 and 1.13-1.25 (two m, CH$_2$CH$_2$CH$_2$CH$_3$), 1.34 and 1.52 (two m, CH$_2$CH$_2$CH$_2$CH$_3$), 1.78 and 2.11 (ddd and dd, 4-CH$_2$), 2.21 and 2.61 (two d, 3-CH$_2$), 2.84 and 2.97 (dd and ddd, 5-CH$_2$), 6.67 (d, H-6), 6.78 (dd, H-8), and 8.37 (d, H-9).

EXAMPLE 6

Synthesis of 6-Bromo-3a-Butyl-7-Hydroxy-1-Methyl-3,3a,4,5-Tetrahydro-2H-Cyclopenta[a]Naphthalen-2-One

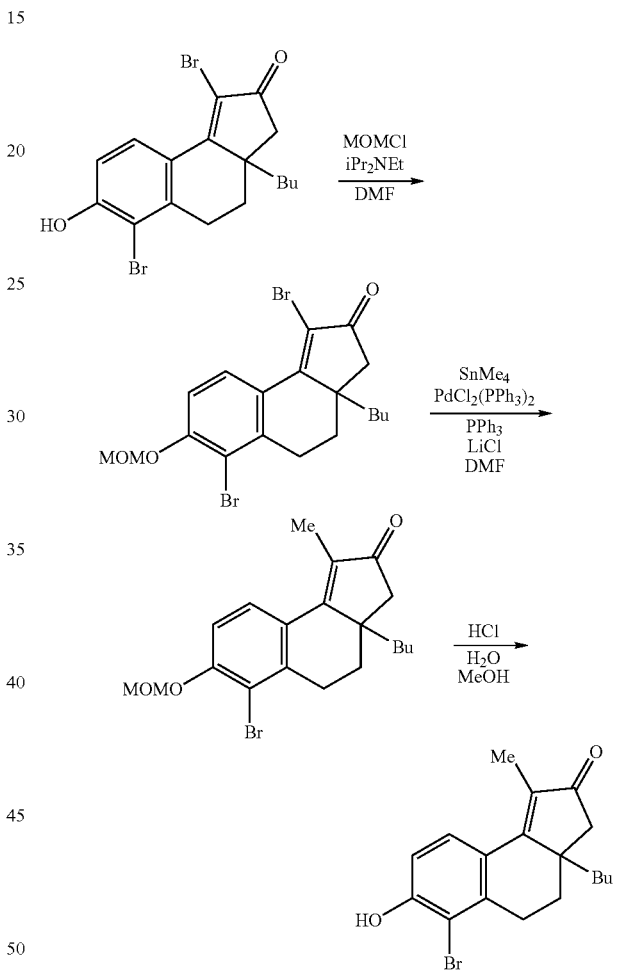

Step 1: 1,6-dibromo-3a-butyl-7-(methoxymethoxy)-3,3a,4,5-tetrahydro-2H-cyclopenta[a]naphthalen-2-one A solution of 1,6-dibromo-3a-butyl-7-hydroxy-3,3a,4,5-tetrahydro-2H-cyclopenta[a]naphthalen-2-one (189 mg, 0.46 mmol) in anhydrous DMF (2.3 mL) was placed under a N$_2$ atmosphere and stirred at room temperature while N,N-diisopropylethylamine (0.242 mL, 1.38 mmol) and chloromethyl methyl ether (0.070 mL, 0.92 mmol) were added successively. After stirring at room temperature for 16 hours, the mixture was diluted with EtOAc and washed with 1N HCl. The organic phase was washed with 5% NaHCO$_3$ and brine, dried over MgSO$_4$, filtered, and concentrated under vacuum to provide crude 1,6-dibromo-3a-butyl-7-(methoxymethoxy)-3,3a,4,5-tetrahydro-2H-cyclopenta[a]naphthalen-2-one as an oil.

Step 2: 6-bromo-3a-butyl-7-(methoxymethoxy)-1-methyl-3,3a,4,5-tetrahydro-2H-cyclopenta[a]naphthalen-2-one A mixture of 1,6-dibromo-3a-butyl-7-(methoxymethoxy)-3,3a,4,5-tetrahydro-2H-cyclopenta[a]naphthalen-2-one (71 mg, 0.15 mmol), dichlorobis(triphenylphosphine)palladium (II) (16 mg, 0.022 mmol), tetramethyltin (0.053 mL, 0.36 mmol), lithium chloride (13 mg, 0.30 mmol), and triphenylphosphine (8 mg, 0.03 mmol) in anhydrous N,N-dimethylformamide (DMF, 0.75 mL) was placed under a $N_2$ atmosphere and heated in an oil bath at 100° C. for 2 days. After cooling, the mixture was concentrated under vacuum, the residue was taken up in $CHCl_3$ and filtered through a pad of silica gel, and the filtrate was evaporated under vacuum to provide an oil. This material was purified by preparative layer chromatography on a 0.1×20×20 cm silica gel GF plate (Analtech, Newark, Del.), developing with 2:1 hexane-EtOAc. The UV visible band at $R_f$ 0.44-0.50 was eluted with EtOAc and the eluant evaporated under vacuum to provide 6-bromo-3a-butyl-7-(methoxymethoxy)-1-methyl-3,3a,4,5-tetrahydro-2H-cyclopenta[a]naphthalen-2-one contaminated with approximately 10% of 3a-butyl-7-(methoxymethoxy)-1,6-dimethyl-3,3a,4,5-tetrahydro-2H-cyclopenta[a]naphthalen-2-one.

Step 3: 6-bromo-3a-butyl-7-hydroxy-1-methyl-3,3a,4,5-tetrahydro-2H-cyclopenta[a]naphthalen-2-one The product mixture from step 2 (18 mg, 0.046 mmol) was dissolved in methanol (1 mL) and treated with aqueous 2N HCl (0.069 mL, 0.137 mmol) at 60° C. The mixture was placed under a $N_2$ atmosphere and heated in an oil bath at 80° C. for 40 minutes. After cooling, the mixture was diluted with EtOAc, washed with 5% $NaHCO_3$ and brine, dried over $MgSO_4$, filtered, and evaporated under vacuum. The residue was purified by preparative layer chromatography on a 0.1× 20×20 cm silica gel GF plate (Analtech, Newark, Del.), developing three times with 2:1 hexane-EtOAc, to give a mixture of 6-bromo-3a-butyl-7-hydroxy-1-methyl-3,3a,4,5-tetrahydro-2H-cyclopenta[a]naphthalen-2-one and 3a-butyl-7-hydroxy-1,6-dimethyl-3,3a,4,5-tetrahydro-2H-cyclopenta[a]naphthalen-2-one. The mixture was resolved by preparative HPLC on a YMC PAK ODS column (100 mm×20 mm id, YMC Co., Ltd. Japan), eluting with a 40-50-100% $MeCN/H_2O$ gradient at 20 mL/min. The product-containing fractions were combined, evaporated under vacuum, and the residue rinsed with EtOAc (2×0.1 mL) to provide 6-bromo-3a-butyl-7-hydroxy-1-methyl-3,3a,4,5-tetrahydro-2H-cyclopenta[a]naphthalen-2-one as a white solid.

$^1$H NMR ($CDCl_3$, 500 MHz) δ 0.81 (t, $CH_2CH_2CH_2CH_3$), 0.98-1.07, 1.15-1.30, and 1.47 (three m, $CH_2CH_2CH_2CH_3$), 1.74 and 2.27 (ddd and dd, 4-$CH_2$), 1.99 (s, 1-$CH_3$), 2.14 and 2.55 (two d, 3-$CH_2$), 2.82 and 2.97 (ddd and dd, 5-$CH_2$), 7.02 (d, H-8), and 7.55 (d, H-9).

EXAMPLE 7

Synthesis of 3a-Butyl-7-Hydroxy-1,6-Dimethyl-3,3a,4,5-Tetrahydro-2H-Cyclopenta[a]Naphthalen-2-One

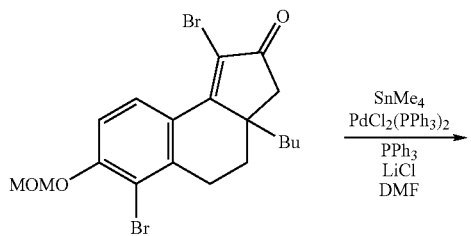

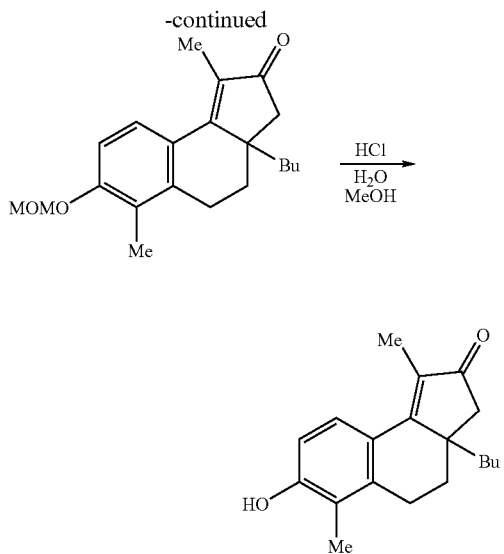

Step 1: 3a-butyl-7-(methoxymethoxy)-1,6-dimethyl-3,3a,4,5-tetrahydro-2H-cyclopenta[a]naphthalen-2-one A mixture of 1,6-dibromo-3a-butyl-7-(methoxymethoxy)-3,3a,4,5-tetrahydro-2H-cyclopenta[a]naphthalen-2-one (139 mg, 0.30 mmol), dichlorobis(triphenylphosphine)palladium (II) (23 mg, 0.03 mmol), lithium chloride (25 mg, 0.60 mmol), triphenylphosphine (16 mg, 0.06 mmol), and anhydrous N,N-dimethylformamide (DMF, 0.6 mL) was purged with $N_2$ and treated with tetramethyltin (0.416 mL, 3.0 mmol). The mixture was stirred under a $N_2$ atmosphere and heated at 100° C. for 22 hours. After cooling, the mixture was concentrated under vacuum, the residue was diluted with EtOAc and filtered through a pad of silica gel, and the filtrate was evaporated under vacuum to provide an oil. The crude product was purified by Biotage™ (Charlottesville, Va.) flash chromatography on a 12S (1.2×7.5 cm) silica gel column, eluting with 10:1 hexane-EtOAc (50 mL) followed by 4:1 hexane-EtOAc (100 mL). The product-containing fractions were evaporated under vacuum to afford 3a-butyl-7-(methoxymethoxy-1,6-dimethyl-3,3a,4,5-tetrahydro-2H-cyclopenta[a]naphthalen-2-one as an oil.

Step 2: 3a-butyl-7-hydroxy-1,6-dimethyl-3,3a,4,5-tetrahydro-2H-cyclopenta[a]naphthalen-2-one A solution of 3a-butyl-7-(methoxymethoxy)-1,6-dimethyl-3,3a,4,5-tetrahydro-2H-cyclopenta[a]naphthalen-2-one (63 mg, 0.19 mmol) in methanol (1.1 mL) was treated with aqueous 2N HCl (0.3 mL), placed under a $N_2$ atmosphere, stirred, and heated in an oil bath at 80° C. for 35 minutes. After cooling, the mixture was diluted with EtOAc (25 mL) and washed with 5% NaHCO3 (10 mL). The organic phase was dried over MgSO4, filtered, and evaporated under vacuum to provide 3a-butyl-7-hydroxy-1,6-dimethyl-3,3a,4,5-tetrahydro-2H-cyclopenta[a]naphthalen-2-one as a solid.

$^1$H NMR ($CDCl_3$, 500 MHz) δ 0.81 (t, $CH_2CH_2CH_2CH_3$), 1.00-1.08, 1.15-1.31, and 1.48 (three m, $CH_2CH_2CH_2CH_3$), 1.72 and 2.26 (two ddd, 4-$CH_2$), 1.99 (s, 1-$CH_3$), 2.13 and 2.53 (two d, 3-$CH_2$), 2.18 (s, 6-$CH_3$), 2.76 and 2.84 (two ddd, 5-$CH_2$), 5.15 (br s, OH), 6.77 (d, H-8), and 7.41 (d, H-9); mass spectrum m/z 285.2 (M+1).

EXAMPLE 8

Synthesis of 3a-Butyl-7-Hydroxy-1-Methyl-3,3a,4,5-Tetrahydro-2H-Cyclopenta[a]Naphthalen-2-One

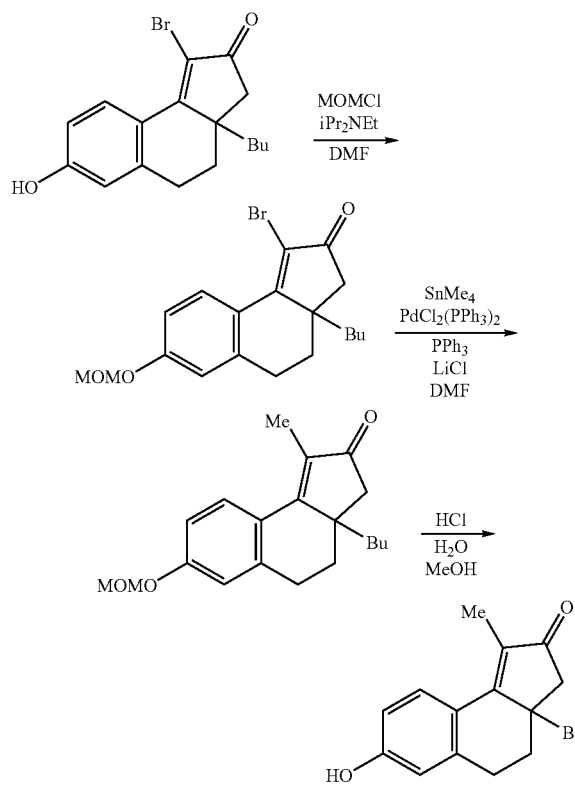

Step 1: 1-bromo-3a-butyl-7-(methoxymethoxy)-3,3a,4,5-tetrahydro-2H-cyclopenta[a]naphthalen-2-one A solution of crude 1-bromo-3a-butyl-7-hydroxy-3,3a,4,5-tetrahydro-2H-cyclopenta[a]naphthalen-2-one (120 mg, contains ~20% of the 1,6 dibromo intermediate) in anhydrous N,N-dimethylformamide (1.8 mL) was placed under a $N_2$ atmosphere and stirred at room temperature while N,N-diisopropylethylamine (0.35 mL, 1.98 mmol) and chloromethyl methyl ether (0.099 mL, 1.3 mmol) were added successively. After stirring overnight at room temperature, the mixture was diluted with EtOAc (125 mL) and washed with 1N HCl (60 mL). The aqueous phase was back-extracted with EtOAc (75 mL). The combined organics were washed with 5% $NaHCO_3$ (60 mL) and brine (60 mL), dried over $MgSO_4$, filtered, and concentrated under vacuum to an oil. The crude product mixture was purified by Biotage™ (Charlottesville, Va.) flash chromatography on a 12M (1.2×15 cm) silica gel column, eluting with 10:1 hexane-EtOAc. Early fractions provided 1,6-dibromo-3a-butyl-7-(methoxymethoxy)-3,3a,4,5-tetrahydro-2H-cyclopenta[a]naphthalen-2-one and later fractions provided 1-bromo-3a-butyl-7-(methoxymethoxy)-3,3a,4,5-tetrahydro-2H-cyclopenta[a]naphthalen-2-one.

Step 2: 3a-butyl-7-(methoxymethoxy)-1-methyl-3,3a,4,5-tetrahydro-2H-cyclopenta[a]naphthalen-2-one A mixture of 1-bromo-3a-butyl-7-(methoxymethoxy)-3,3a,4,5-tetrahydro-2H-cyclopenta[a]naphthalen-2-one (78 mg, 0.20 mmol), dichlorobis(triphenylphosphine)palladium (II) (7 mg, 0.01 mmol), and triphenylphosphine (5 mg, 0.02 mmol) in anhydrous N,N-dimethylformamide (DMF, 0.6 mL) was placed under a $N_2$ atmosphere, treated with tetramethyltin (0.042 mL, 0.29 mmol), and heated in an oil bath at 100° C. for 21.5 hours. Additional dichlorobis(triphenylphosphine)palladium(II) (6 mg, 009 mmol) and tetramethyltin (0.042 mL, 0.29 mmol) were added and the mixture was heated at 100° C. overnight. After cooling, the mixture was concentrated under vacuum, the residue was taken up in EtOAc and filtered through a pad of $MgSO_4$ atop silica gel, and the filtrate was evaporated under vacuum. The residue was treated with dichlorobis(triphenylphosphine)palladium (II), triphenylphosphine, DMF, and tetramethyltin as described above for the original conditions, and the mixture was heated at 100° C. under $N_2$ for 23 hours. Workup afforded an oil which was shown to be a 3-4:1 mixture of 3a-butyl-7-(methoxymethoxy)-1-methyl-3,3a,4,5-tetrahydro-2H-cyclopenta[a]naphthalen-2-one and starting material by NMR.

Step 3: 3a-butyl-7-hydroxy-1-methyl-3,3a,4,5-tetrahydro-2H-cyclopenta[a]naphthalen-2-one A portion of the product mixture from step 2 (32 mg, ~0.96 mmol) was dissolved in methanol (0.5 mL) and treated with aqueous 2N HCl (0.15 mL, 0.3 mmol). The mixture was placed under a $N_2$ atmosphere and heated in an oil bath at 80° C. for 55 minutes. After cooling, the mixture was diluted with EtOAc, washed with 5% $NaHCO_3$ and brine, dried over $MgSO_4$, filtered, and evaporated under vacuum to a gum. The product mixture was purified by preparative HPLC on a YMC PAK ODS column (100 mm×20 mm id, YMC Co., Ltd. Japan), eluting with a 25 to 50 to 100% $MeCN/H_2O$ gradient, to give pure 3a-butyl-7-hydroxy-1-methyl-3,3a,4,5-tetrahydro-2H-cyclopenta[a]naphthalen-2-one.

$^1$H NMR ($CDCl_3$, 500 MHz) δ 0.81 (t, $CH_2CH_2CH_2CH_3$), 1.01-1.11, 1.15-1.31, and 1.52 (three m, $CH_2CH_2CH_2CH_3$), 1.73 and 2.17 (ddd and dd, 4-$CH_2$), 2.01 (s, 1-$CH_3$), 2.15 and 2.56 (two d, 3-$CH_2$), 2.86 and 3.00 (dd and ddd, 5-$CH_2$), 6.76 (d, H-6), 6.83 (dd, H-8), and 7.56 (d, H-9); mass spectrum m/z 271.1 (M+1).

EXAMPLE 9

Synthesis of 1-Bromo-3A-Butyl-6-Chloro-8-Fluoro-7-Hydroxy-3,3A,4,5-Tetrahydro-2H-Cyclopenta[a]Naphthalen-2-One

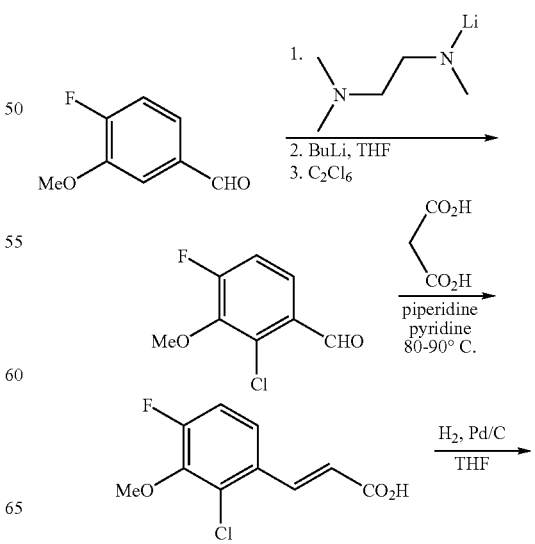

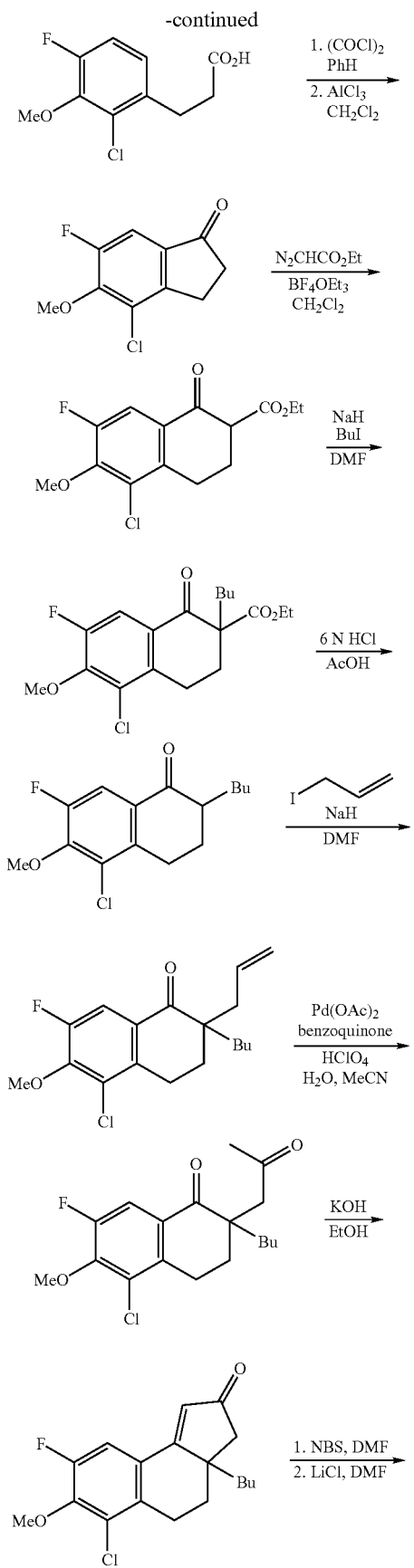

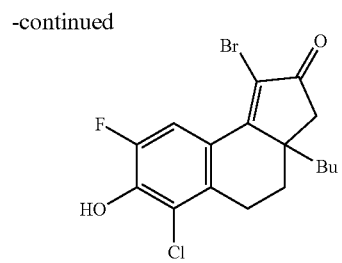

Step 1: 2-chloro-4-fluoro-3-methoxybenzaldehyde

A solution of N,N,N'-trimethylethylenediamine (20.3 mL, 156 mmol) in 75 mL of THF was cooled to −50° C. and a 2.5M solution of n-butyllithium in hexanes (62.5 mL, 156 mmol) was added dropwise with stirring during 15 minutes, keeping the internal temperature below −35° C. The temperature was maintained at 40° C. for 30 minutes, and then the reaction mixture was cooled to −70° C. A solution of 4-fluoro-3-methoxybenzaldehyde (24.09 g, 156.3 mmol) in 75 mL of THF was added dropwise during 15 minutes, keeping the reaction temperature below −50° C. When the addition was complete, the reaction was allowed to warm to −40° C. and held there for 25 minutes. The reaction was then re-cooled to −70° C. and a 2.5M solution of n-butyllithium in hexanes (62.5 mL, 156 mmol) was added dropwise. When the addition was complete, the reaction was allowed to warm to −20° C. and kept at that temperature overnight (12 hours). The reaction mixture was then cooled to −30° C. and the cold solution was added via cannula during 30 minutes to a room temperature solution of hexachloroethane (111 g, 469 mmol) in 200 mL of THF. After stirring at room temperature for 4 hours, the reaction mixture was poured into 500 mL of ice cold 4N HCl. Most of the THF was removed by rotary evaporation under reduced pressure and the residual mixture was extracted twice with 1:1 ethyl ether/hexanes. The organic layers were combined and washed successively with 1N NaOH, 1N HCl, water, and brine. After drying over sodium sulfate, removal of the solvent under vacuum gave a yellow solid. Flash chromatography on silica gel eluting with hexanes/dichloroethane (2:1 to 1:1) gave 2-chloro-4-fluoro-3-methoxybenzaldehyde as a white solid.

Step 2: (2E)-3-(2-chloro-4-fluoro-3-methoxyphenyl)acrylic acid

To a mixture of 2-Chloro-4-fluoro-3-methoxybenzaldehyde (17.6 g, 93.3 mmol) and malonic acid (18.6 g, 179 mmol) was added pyridine (60 mL) followed by piperidine (1.6 mL, 19 mmol). The mixture was heated in a 90° C. oil bath giving a clear yellow solution. After 220 minutes, the hot solution was poured into 500 mL of ice cold 2.5N HCl with stirring. The resulting solid was isolated by filtration, washing thoroughly with water. Drying under vacuum gave (2E)-3-(2-chloro-4-fluoro-3-methoxyphenyl)acrylic acid as a yellow solid.

Step 3: 3-(2-chloro-4-fluoro-3-methoxyphenyl)propanoic acid

A solution of (2E)-3-(2-chloro-4-fluoro-3-methoxyphenyl)acrylic acid (20.3 g, 88 mmol) in 800 mL of THF and 200 mL of methanol was hydrogenated over 1.2 g of 10% Pd/C under balloon pressure of hydrogen. After 105 minutes, an additional 1 g of 10% Pd/C was added. After a total of 6 hours, the reaction mixture was filtered through a pad of Celite, washing with THF and EtOAc. Evaporation under vacuum gave 3-(2-cChloro-4-fluoro-3-methoxyphenyl)propanoic acid as a pale yellow solid.

Step 4: 4-chloro-6-fluoro-5-methoxyindanone

To a solution of 3-(2-chloro-4-fluoro-3-methoxyphenyl) propanoic acid (20.74 g, 88 mmol) in benzene (440 mL) was added DMF (0.14 mL, 1.8 mmol) followed by gradual addition of oxalyl chloride (15.4 mL, 177 mmol) during 25 minutes. After 2 hours, the reaction mixture was evaporated under vacuum to give a yellow oil. The oil was dissolved in 100 mL of benzene and evaporated under vacuum. This process was then repeated. The resulting oil was dissolved in dichloromethane (500 mL) and solid aluminum chloride (12.9 g, 96.7 mmol) was added during 5 minutes using a solid addition funnel. After 20 minutes, the reaction mixture was poured onto ca 1000 cc of ice. When most of the ice had melted, the layers were separated and the aqueous phase was extracted with dichloromethane. The combined organic layers were washed successively with 2N HCl, water and brine. After drying over sodium sulfate, the solution was evaporated under vacuum to give a yellow solid. Flash chromatography through silica gel eluting with EtOAc/hexanes/dichloromethane (10:95:95) gave 4-chloro-6-fluoro-5-methoxyindanone as a white solid.

Step 5: ethyl 5-chloro-7-fluoro-6-methoxy-1-oxo-1,2,3,4-tetrahydronaphthalene-2-carboxylate 4-chloro-6-fluoro-5-methoxyindanone (2.14 g, 10.0 mmol) was dissolved in dichloromethane (10 mL), cooled in an ice bath, and treated with triethyloxonium tetrafluoroborate (30 mmol, 30 mL of a 1M solution in dichloromethane) and stirred at 0° C. for ten minutes under an atmosphere of $N_2$. Ethyl diazoacetate (1.6 mL, 15 mmol) was then added via syringe pump during 35 minutes to give an orange solution. Following the addition, the cooling bath was removed and the reaction stirred for 16 hours. The reaction was quenched with saturated aqueous $Na_2CO_3$ (50 ml) then extracted twice with 75 mL portions of dichloromethane. The combined organic extracts were dried over $MgSO_4$, filtered and concentrated in vacuo to give 3.75 g of an orange oil. The crude product was purified by Biotage™ (Charlottesville, Va.) flash chromatography on a 40M (4×15 cm) silica gel column, eluting successively with 1000 mL portions of 5% then 10% EtOAc in hexane. The product-containing fractions were combined and evaporated under vacuum to give ethyl 5-chloro-7-fluoro-6-methoxy-1-oxo-1,2,3,4-tetrahydronaphthalene-2-carboxylate which appeared as a mixture of enols by $^1H$ NMR.

Step 6: ethyl 2-butyl-5-chloro-7-fluoro-6-methoxy-1-oxo-1,2,3,4-tetrahydronaphthalene-2-carboxylate Ethyl 5-chloro-7-fluoro-6-methoxy-1-oxo-1,2,3,4-tetrahydronaphthalene-2-carboxylate (651 mg, 2.17 mmol) was dissolved in dimethylformamide (DMF, 2.2 mL) with gentle heating. After cooling to room temperature, sodium hydride (160 mg, 61% dispersion in mineral oil, 4.0 mmol) was added to give a black solution which was placed under $N_2$. Iodobutane (1.15 mL, 10 mmol) was added and the reaction stirred at room temperature for 19 hours. The reaction mixture was then partitioned between EtOAc/$H_2O$ and the organic portion was washed with brine, dried over $MgSO_4$, filtered and evaporated under vacuum. The crude product was purified by Biotage™ (Charlottesville, Va.) flash chromatography on a 40S (4×7.5 cm) silica gel column, eluting with 1000 mL of 2% EtOAc in hexane. The product-containing fractions were concentrated to give ethyl 2-butyl-5-chloro-7-fluoro-6-methoxy-1-oxo-1,2,3,4-tetrahydronaphthalene-2-carboxylate.

Step 7: 2-butyl-5-chloro-7-fluoro-6-methoxy-3,4-dihydro-2H-naphthalen-1-one 2-butyl-5-chloro-7-fluoro-6-methoxy-1-oxo-1,2,3,4-tetrahydro-naphthalene-2-carboxylic acid ethyl ester (263 mg, 0.74 mmol) was dissolved in AcOH (6 mL) then treated with 6N HCl (6 mL). This solution was heated with stirring at 80° C. for 75 minutes, then at 100° C. for 2 hours. After cooling to room temperature the mixture was partitioned between EtOAc/5% $NaHCO_3$. The organic phase was washed with brine, dried over $MgSO_4$, filtered and evaporated under vacuum. Two successive purifications of the crude product by Biotage™ (Charlottesville, Va.) flash chromatography on a 40S (4×7.5 cm) silica gel columns, eluting with EtOAc/hexane yielded 2-butyl-5-chloro-7-fluoro-6-methoxy-3,4-dihydro-2H-naphthalen-1-one and recovered starting material.

Step 8: 2-allyl-2-butyl-5-chloro-7-fluoro-6-methoxy-3,4-dihydro-2H-naphthalen-1-one Sodium hydride (15 mg, 61% dispersion in mineral oil, 0.38 mmol) was placed in a flame dried flask, then washed with hexanes to remove mineral oil, and finally suspended in DMF (0.3 mL) under an atmosphere of $N_2$. A solution of 2-butyl-5-chloro-7-fluoro-6-methoxy-3,4-dihydro-2H-naphthalen-1-one (54 mg in 0.2 mL DMF, 0.19 mmol) was added at room temperature to give a bright yellow reaction mixture. After five minutes, allyl iodide (0.055 mL, 0.6 mmol) was added. The reaction was stirred for 1.5 hours, then partitioned between EtOAc/$H_2O$. The organic phase was washed twice with water, dried over $MgSO_4$, filtered and then evaporated under vacuum. The crude product was purified by preparative layer chromatography on a 0.1×20×20 cm silica gel GF plate (Analtech, Newark, Del.), developing with 10:1 hexane-EtOAc. The product band at $R_f$ 0.45-0.55 was eluted with 5% MeOH in $CH_2Cl_2$ and concentrated under vacuum to give 2-allyl-2-butyl-5-chloro-7-fluoro-6-methoxy-3,4-dihydro-2H-naphthalen-1-one as an oil.

Step 9: 2-butyl-5-chloro-7-fluoro-6-methoxy-2-(2-oxopropyl)-3,4-dihydro-2H-naphthalen-1-one 2-allyl-2-butyl-5-chloro-7-fluoro-6-methoxy-3,4-dihydro-2H-naphthalen-1-one (40 mg, 0.12 mmol) was dissolved in acetonitrile (0.36 mL) and treated with benzoquinone (20 mg, 0.18 mmol), Pd(OAc)$_2$ (5 mg. 0.02 mmol), water (0.018 mL) and perchloric acid (70%, 0.005 mL) to give an orange solution. This solution was stirred under an air atmosphere for 16.5 hours, then purified by preparative layer chromatography on a 0.1×20×20 cm silica gel GF plate (Analtech, Newark, Del.), developing with 4:1 hexane-EtOAc. The band at $R_f$ 0.53-0.59 was eluted with 5% MeOH in $CH_2Cl_2$ to give 2-butyl-5-chloro-7-fluoro-6-methoxy-2-(2-oxopropyl)-3,4-dihydro-2H-naphthalen-1-one as a slightly yellow oil.

Step 10: 3a-butyl-6-chloro-8-fluoro-7-methoxy-3,3a,4,5-tetrahydro-2H-cyclopenta[a]naphthalen-2-one To a solution of 2-butyl-5-chloro-7-fluoro-6-methoxy-2-(2-oxo-propyl)-3,4-dihydro-2H-naphthalen-1-one (28 mg, 0.08 mmol) in EtOH (0.4 mL) was added potassium hydroxide (2M solution in EtOH, 0.05 mL, 0.1 mmol). The reaction mixture was heated at 90° C. in a sealed flask for two hours. The reaction was cooled to room temperature, diluted with dichloromethane (5 mL) and filtered through a pad of $MgSO_4$ atop a pad of $SiO_2$. The filter pad was washed with 5% MeOH in $CH_2Cl_2$ and the combined filtrates concentrated under vacuum to give 3a-butyl-6-chloro-8-fluoro-7-methoxy-3,3a,4,5-tetrahydro-2H-cyclopenta[a]naphthalen-2-one as an oil which solidified on standing.

Step 11: 1-bromo-3a-butyl-6-chloro-8-fluoro-7-hydroxy-3,3a,4,5-tetrahydro-2H-cyclopenta[a]naphthalen-2-one A solution of 3a-butyl-6-chloro-8-fluoro-7-methoxy-3,3a,4,5-tetrahydro-cyclopenta[a]naphthalen-2-one (22 mg, 0.07 mmol) in DMF (0.12 mL) was treated with N-bromosuccinimide (12 mg, 0.07 mmol) at room temperature under $N_2$ for 100 minutes, after which very little reaction had occurred. The reaction was thus heated to 60° C. for 50 minutes, then diluted with DMF (0.5 mL). Lithium chloride (29 mg, 0.68 mmol) was added and the reaction was heated to 100° C. After stirring at 100° C. for 1.5 hours the reaction was heated at 120° C. for 50 minutes. The reaction was cooled to room temperature and then partitioned between EtOAc/H₂O. The organic portion was washed several times with water, then with brine, dried over MgSO₄, filtered and then concentrated under vacuum. The crude material was purified by preparative layer chromatography on a 0.05×20×20 cm silica gel GF plate (Analtech, Newark, Del.), developing with 2.5% MeOH in CH₂Cl₂. The low $R_f$ band was eluted with 5% MeOH in CH₂Cl₂ and concentrated under vacuum to give 1-bromo-3a-butyl-6-chloro-8-fluoro-7-hydroxy-3,3a,4,5-tetrahydro-2H-cyclopenta[a]naphthalen-2-one as an off-white film.

¹HNMR (CDCl₃, 500 MHz) δ 0.83 (t, CH₂CH₂CH₂CH₃), 1.02-1.08, 1.19-1.29, 1.31-1.37, and 1.48-1.54 (four m, CH₂CH₂CH₂CH₃), 1.83 and 2.27 (ddd and dd, 4-CH₂), 2.27 and 2.68 (two d, 3-CH₂), 2;81 and 3.02 (dddd and dd, 5-CH₂), 6.04 (d, OH), and 8.27 (d, H-9) mass spectrum m/z 387.3 (M+1), 389.3, 391.3.

EXAMPLE 10

Synthesis of 10a-Butyl-7-Hydroxy-1,9,10,10a-Tetrahydro-3(2H)-Phenanthrenone

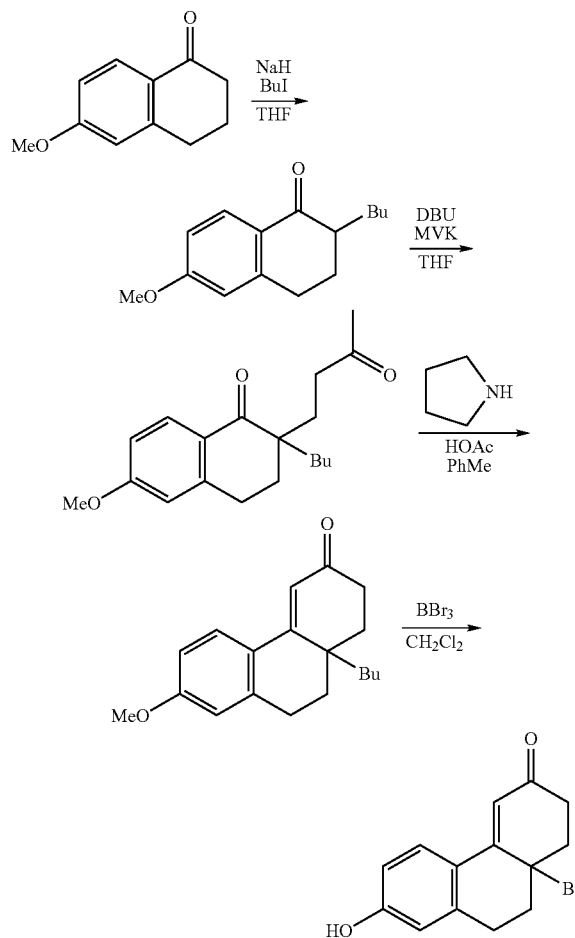

Step 1: 2-butyl-6-methoxy-3,4-dihydro-1(2H)-naphthalenone

A mixture of 6-methoxy-3,4-dihydro-1(2H)-naphthalenone (400 mg, 2.27 mmol), iodobutane (0.284 mL, 2.5 mmol), NaH (98 mg of a 61.1% dispersion in mineral oil, 2.5 mmol), and anhydrous tetrahydrofuran (THF, 1 mL) was placed under a N₂ atmosphere and stirred at room temperature for 15.5 hours. The mixture was partitioned between EtOAc (20 mL) and water (30 mL) containing 2N HCl (3 mL). The organic phase was washed with brine (20 mL), dried over MgSO₄, filtered, and evaporated under vacuum to afford an oil. The crude product was purified by preparative layer chromatography on five 0.1×20×20 cm silica gel GF plates (Analtech, Newark, Del.), developing with CH₂Cl₂. The UV visible product band was eluted with EtOAc and the eluant evaporated under vacuum to provide 2-butyl-6-methoxy-3,4-dihydro-1(2H)-naphthalenone as a clear oil.

Step 2: 2-butyl-6-methoxy-2-(3-oxobutyl)-3,4-dihydro-1(2H)-naphthalenone

A solution of 2-butyl-6-methoxy-3,4-dihydro-1(2H)-naphthalenone (230 mg, 1 mmol) in anhydrous tetrahydrofuran (THF, 0.5 mL) was placed under a N₂ atmosphere and treated with 1,8-diazabicyclo[5.4.0]undec-7-ene (DBU, 0.037 mL, 0.25 mmol) followed by methyl vinyl ketone (MVK, 0.104 mL, 1.25 mmol). The mixture was stirred at room temperature for 19 hours and then heated at 60° C. for 80 minutes. Additional MVK (0.104 mL, 1.25 mmol) was added and the mixture was stirred at 60° C. for 2.5 hours. Additional DBU (0.037 mL, 0.25 mmol) was then added and the mixture was stirred at 60° C. for 70 minutes. After cooling to room temperature, the mixture was concentrated under a stream of N₂ and the residue was purified by preparative layer chromatography on three 0.1×20×20 cm silica gel GF plates (Analtech, Newark, Del.), developing with 5% EtOAc in CH₂Cl₂. The UV visible product band was eluted with EtOAc and the eluant was evaporated under vacuum to provide 2-butyl-6-methoxy-2-(3-oxobutyl)-3,4-dihydro-1(2H)-naphthalenone as an oil.

Step 3: 10a-butyl-7-methoxy-1,9,10,10a-tetrahydro-3(2H)-phenanthrenone

A mixture of 2-butyl-6-methoxy-2-(3-oxobutyl)-3,4-dihydro-1(2H)-naphthalenone (91 mg, 0.3 mmol), pyrrolidine (0.025 mL, 0.3 mol), acetic acid (0.017 mL, 0.3 mmol), and toluene (0.5 mL) was stirred and heated in an oil bath at 100° C. for 3 hours. After standing at room temperature overnight, the mixture was partitioned between EtOAc (20 mL) and water (20 mL) containing 2N HCl (2 mL). The organic phase was washed with 5% NaHCO₃ (10 mL) and brine (10 mL), dried over MgSO₄, filtered, and concentrated under vacuum. The residue was purified by preparative layer chromatography on a 0.1×20×20 cm silica gel GF plate (Analtech, Newark, Del.), developing with 5% EtOAc in CH₂Cl₂. The UV visible product band was eluted with EtOAc and the eluant was evaporated under vacuum to provide 10a-butyl-7-methoxy-1,9,10,10a-tetrahydro-3(2H)-phenanthrenone as a clear oil.

Step 4: 10a-butyl-7-hydroxy-1,9,10,10a-tetrahydro-3(2H)-phenanthrenone

A solution of 10a-butyl-7-methoxy-1,9,10,10a-tetrahydro-3(2H)-phenanthrenone (16 mg, 0.056 mmol) in anhydrous CH₂Cl₂ (0.5 mL) was cooled in an ice bath, stirred, and treated with 1M BBr₃ in CH₂Cl₂ (0.3 mL, 0.3 mmol). The cooling bath was removed and the mixture was stirred at room temperature for 170 minutes. The mixture was partitioned between EtOAc (20 mL) and water (20 mL) containing 2N HCl (2 mL). The organic phase was washed with brine (20 mL), dried over MgSO₄, filtered, and evaporated under vacuum. The residue was purified by preparative layer chromatography on a 0.05×20×20 cm silica gel GF plate (Analtech, Newark, Del.), developing with 5% CH₃OH in CH₂Cl₂. The UV visible product band was eluted with 10% CH₃OH in $CH_2Cl_2$ and the eluant was evaporated under vacuum to provide 10a-butyl-7-hydroxy-1,9,10,10a-tetrahydro-3(2H)-phenanthrenone as an oil.

$^1H$ NMR (DMSO-$d_6$, 500 MHz) δ 0.85 (t, $CH_2CH_2CH_2CH_3$), 1.20-1.33 (m, $CH_2CH_2CH_2CH_3$), 1.36 and 1.42 (two m, $CH_2CH_2CH_2CH_3$), 1.48, 1.63, 1.87, and 2.01 (four ddd, 1-$CH_2$ and 10-$CH_2$), 2.20 and 2.46 (two ddd, 2-$CH_2$), 2.68 and 2.79 (two ddd, 9-$CH_2$), 6.26 (s, H-4), 6.58 (d, H-8), 6.65 (dd, H-6), 7.65 (d, H-5), and 9.93 (s, OH).

EXAMPLE 11

Synthesis of 4-Bromo-10a-Butyl-7-Hydroxy-1,9,10,10a-Tetrahydro-3(2H)-Phenanthrenone

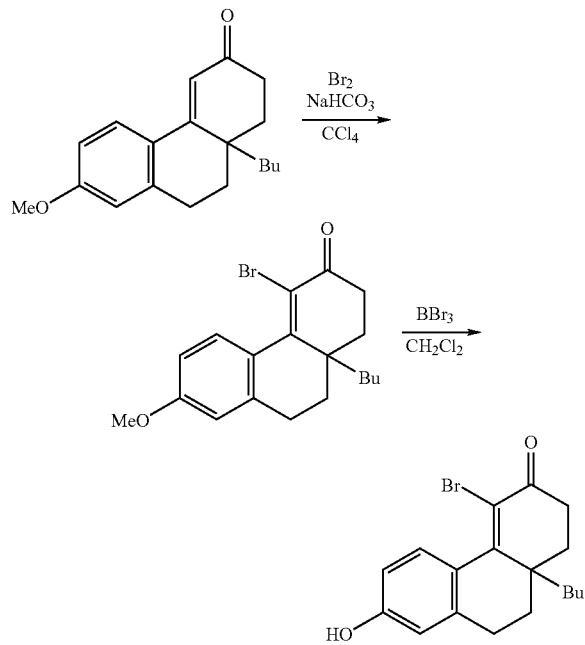

Step 1: 4-bromo-10a-butyl-7-methoxy-1,9,10,10a-tetrahydro-3(2H)-phenanthrenone

A mixture of 10a-butyl-7-methoxy-1,9,10,10a-tetrahydro-3(2H)-phenanthrenone (31 mg, 0.109 mmol) and $NaHCO_3$ (46 mg, 0.545 mmol) in $CCl_4$ (0.25 mL) was stirred at room temperature while $Br_2$ (0.0056 mL, 0.109 mmol) was added by syringe. A gummy precipitate formed which slowly dissolved. After stirring at room temperature for 15 minutes, the mixture was partitioned between EtOAc (4 mL) and aqueous $Na_2SO_3$ (4 mL). The organic phase was washed with brine, dried over $MgSO_4$, filtered, and evaporated under vacuum to an oil. The crude product was purified by preparative layer chromatography on a 0.1×20×20 cm silica gel GF plate (Analtech, Newark, Del.), developing with 5% EtOAc in $CH_2Cl_2$. The UV visible product band was eluted with EtOAc and the eluant was evaporated under vacuum to provide 4-bromo-10a-butyl-7-methoxy-1,9,10,10a-tetrahydro-3(2H)-phenanthrenone as an oil.

Step 2: 4-bromo-10a-butyl-7-hydroxy-1,9,10,10a-tetrahydro-3(2H)-phenanthrenone

A solution of 4-bromo-10a-butyl-7-methoxy-1,9,10,10a-tetrahydro-3(2H)-phenanthrenone (18 mg, 0.05 mmol) in anhydrous $CH_2Cl_2$ (0.5 mL) was cooled in an ice bath, stirred, and treated with 1M $BBr_3$ in $CH_2Cl_2$ (0.3 mL, 0.3 mmol). The cooling bath was removed and the mixture was stirred at room temperature for 175 minutes. The mixture was partitioned between EtOAc (20 mL) and water (20 mL) containing 2N HCl (2 mL). The organic phase was washed with brine (20 mL), dried over $MgSO_4$, filtered, and evaporated under vacuum. The residue was purified by preparative layer chromatography on a 0.05×20×20 cm silica gel GF plate (Analtech, Newark, Del.), developing with 5% $CH_3OH$ in $CH_2Cl_2$. The UV visible product band was eluted with 10% $CH_3OH$ in $CH_2Cl_2$ and the eluant was evaporated under vacuum to provide 4-bromo-10a-butyl-7-hydroxy-1,9,10,10a-tetrahydro-3(2H)-phenanthrenone as an oil.

$^1H$ NMR (DMSO-$d_6$, 500 MB), δ 0.77 (t, $CH_2CH_2CH_2CH_3$), 1.10-1.23 and 1.55 (two m, $CH_2CH_2CH_2CH_3$), 1.58, 1.73, 1.86, and 1.97 (four ddd, 1-$CH_2$ and 10-$CH_2$), 2.51 and 2.71 (two ddd, 9-$CH_2$ or 2-$CH_2$), 2.60 (m, 2-$CH_2$ or 9-$CH_2$), 6.61 (d, H-8), 6.65 (dd, H-6), 7.68 (d, H-5), and 9.94 (s, OH).

EXAMPLE 12

Synthesis of 9a-Butyl-2-Hydroxy-5-Methyl-8,9,9a,10-Tetrahydrobenzo[a]Azulen-6(7H)-One

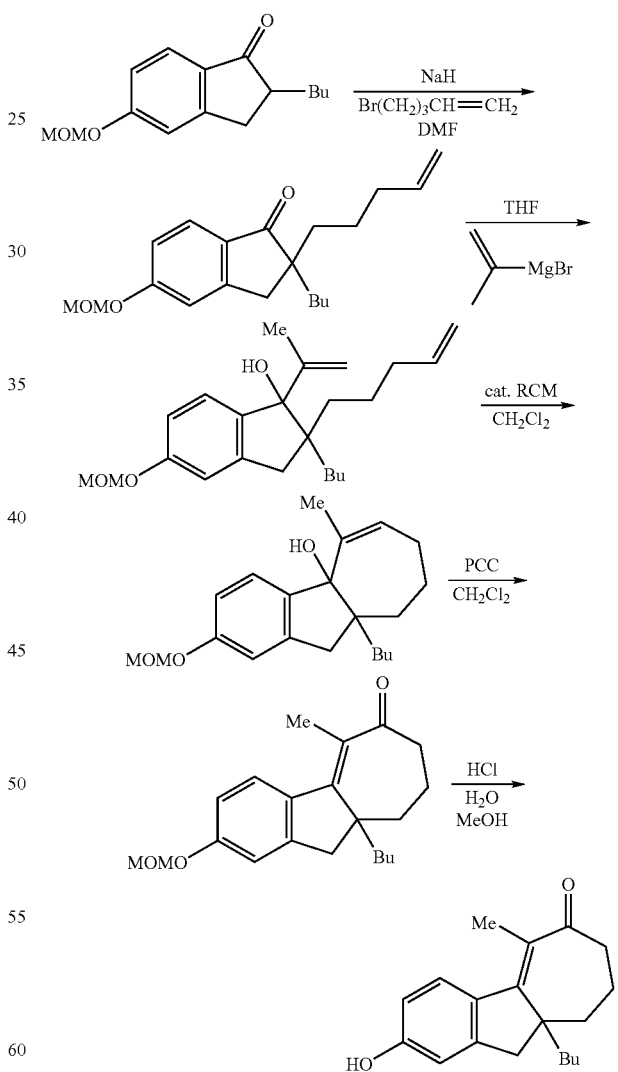

Step 1: 2-butyl-5-(methoxymethoxy)-2-(4-pentenyl)-1-indanone

A solution of 2-butyl-5-(methoxymethoxy)-1-indanone (1.54 g, 6.2 mmol) in anhydrous N,N-dimethylformamide (DMF, 5 mL) was added to a suspension of sodium hydride (372 mg of a 60% dispersion in mineral oil, 9.3 mmol) in DMF (5 mL). The mixture was diluted with more DMF (2 mL, used to rinse in the indanone solution), placed under a nitrogen atmosphere, and stirred at room temperature for 25 minutes. 5-Bromo-1-pentene (1.47 mL, 12.4 mmol) was then added over 5 minutes, during which time the mixture clarified. After stirring at room temperature for an additional 5 hours, the mixture was quenched with saturated NH$_4$Cl, dried over MgSO$_4$, filtered through a pad of silica, and concentrated under vacuum to afford an oil. The crude product was purified by Biotage™ (Charlottesville, Va.) flash chromatography on a 40S (4.0×7.0 cm) silica gel column, eluting with 19:1 hexanes-EtOAc. The product-containing fractions were evaporated under vacuum to afford 2-butyl-5-(methoxymethoxy)-2-(4-pentenyl)-1-indanone as an oil.

Step 2: 2-butyl-1-isopropenyl-5-(methoxymethoxy)-2-(4-pentenyl)-1-indanol

A solution of 2-butyl-5-(methoxymethoxy)-2-(4-pentenyl)-1-indanone (400 mg, 1.27 mmol) in anhydrous tetrahydrofuran (THF, 5 mL) was placed under a N$_2$ atmosphere, cooled in a dry ice-acetone bath, stirred, and treated with 2-propenyl magnesium bromide, (1M in THF, 1.9 mL, 1.9 mmol). After warming to room temperature, the mixture was treated with additional 2-propenyl magnesium bromide (1M in THF, 6 mL, 6 mmol) and stirred at room temperature overnight. The mixture was quenched with saturated aqueous NH$_4$Cl, dried over MgSO$_4$, filtered through a pad of silica, and concentrated under vacuum to afford an oil. The crude product was purified by Biotage™ (Charlottesville, Va.) flash chromatography on a 40S (4.0×7.0 cm) silica gel column, eluting with 19:1 hexanes-EtOAc. The product-containing fractions were evaporated under vacuum to afford 2-butyl-1-isopropenyl-5-(methoxymethoxy)-2-(4-pentenyl)-1-indanol as an oil.

Step 3: 9a-butyl-2-(methoxymethoxy)-5-methyl-8,9,9a,10-tetrahydrobenzo[a]azulen-4b(7H)-ol A solution of 2-butyl-1-isopropenyl-5-(methoxymethoxy)-2-(4-pentenyl)-1-indanol (200 mg, 0.56 mmol) in dichloromethane (22 mL) was treated with tricyclohexylphosphine[1,3-bis(2,4,6-trimethylphenyl)-4,5-dihydro-imidazol-2-ylidene]benzylidene]ruthenium(IV) dichloride (47 mg, 0.056 mmol). After stirring at 45° C. overnight, the mixture was treated with additional tricyclohexylphosphine[1,3-bis(2,4,6-trimethylphenyl)-4,5-dihydro-imidazol-2-ylidene] benzylidene]ruthenium (IV) dichloride (47 mg, 0.056 mmol) and stirred at 45° C. for another 24 hours. The mixture was concentrated and the residue purified by preparative layer chromatography on two 0.1×20×20 cm silica gel GF plates (Analtech, Newark, Del.), developing with 10% EtOAc in hexane. The UV visible product band was eluted with EtOAc and the eluant was evaporated under vacuum to provide 9a-butyl-2-(methoxymethoxy)-5-methyl-8,9,9a,10-tetrahydrobenzo[a]azulen-4b(7H)-ol as an oil.

Step 4: 9a-butyl-2-(methoxymethoxy)-5-methyl-8,9,9a,10-tetrahydrobenzo[a]azulen-6(7H)-one A solution of 9a-butyl-2-(methoxymethoxy)-5-methyl-8,9,9a,10-tetrahydrobenzo[a]azulen-4b(7H)-ol (32 mg, 0.1 mmol) in dichloromethane (1 mL) was treated with pyridinium chlorochromate (PCC, 32 mg, 0.15 mmol). After stirring at room temperature for 5 hours, the mixture was treated with additional PCC (5 mg, 0.023 mmol). The mixture was concentrated and purified by preparative layer chromatography on a 0.1×20×20 cm silica gel GF plate (Analtech, Newark, Del.), developing with 10% EtOAc in hexane. The UV visible product band was eluted with EtOAc and the eluant was evaporated under vacuum to provide 9a-butyl-2-(methoxymethoxy)-5-methyl-8,9,9a,10-tetrahydrobenzo[a]azulen-6(7H)-one as an oil.

Step 5: 9a-butyl-2-hydroxy-5-methyl-8,9,9a,10-tetrahydrobenzo[a]azulen-6(7H)-one A solution of 9a-butyl-2-(methoxymethoxy)-5-methyl-8,9,9a,10-tetrahydrobenzo[a]azulen-6(7H)-one (5 mg) in methanol (1 mL) was treated with aqueous 2N HCl (0.1 mL, 0.2 mmol). After stirring at 65° C. for two hours, the mixture was diluted with dichloromethane (2 mL), treated with solid NaHCO$_3$, and purified by preparative layer chromatography on a 0.1×20×20 cm silica gel GF plate (Analtech, Newark, Del.), developing with 20% EtOAc in hexane. The UV visible product band was eluted with EtOAc and the eluant was evaporated under vacuum to provide 9a-butyl-2-hydroxy-5-methyl-8,9,9a,10-tetrahydrobenzo[a]azulen-6(7H)-one as a foam.

$^1$H NMR (CDCl$_3$, 500 MHz) δ 0.82 (t, CH$_2$CH$_2$CH$_2$CH$_3$), 1.10-1.23 (m, CH$_2$CH$_2$CH$_2$CH$_3$), 1.44 and 1.56 (two m, CH$_2$CH$_2$CH$_2$CH$_3$), 1.84-2.02 (m, 8-CH$_2$ and 9-CH$_2$), 2.16 (s, 5-CH$_3$), 2.63 and 2.84 (two ddd, 7-CH$_2$), 2.74 and 2.91 (two d, 10-CH$_2$), 5.11 (s, OH), 6.72 (m, H-1 and H-3), and 7.49 (d, H-4); mass spectrum m/z 285.3 (M+1).

EXAMPLES 13-24

The following compounds were prepared using methods analogous to those described in the preceding examples:

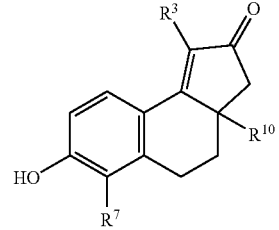

| | | |
|---|---|---|
| 13 | R$^3$ = Br | 1-bromo-7-hydroxy-3a-methyl-3,3a,4,5- |
| | R$^7$ = H | tetrahydro-2H-cyclopenta[α]naphthalen- |
| | R$^{10}$ = CH$_3$ | 2-one |

$^1$H NMR (CDCl$_3$, 500 MHz) δ 1.13 (s, CH$_3$), 1.78 and 1.95 (ddd and dd, 4-CH$_2$), 2.32 and 2.47 (two d, 3-CH$_2$), 2.83 and 2.96 (dd and ddd, 5-CH$_2$), 6.63 (d, H-6), 6.73 (dd, H-8), and 8.36 (d, H-9); mass spectrum m/z 293.0 (M + 1) and 295.0.

| | | |
|---|---|---|
| 14 | R$^3$ = CH$_3$ | 7-hydroxy-1,3a-dimethyl-3,3a,4,5- |
| | R$^7$ = H | tetrahydro-2H-cyclopenta[α]naphthalen- |
| | R$^{10}$ = CH$_3$ | 2-one |

$^1$H NMR (CDCl$_3$, 500 MHz) δ 1.16 (s, 3a-CH$_3$), 1.79 and 2.05 (two ddd, 4-CH$_2$), 2.01 (s, 1-CH$_3$), 2.30 and 2.47 (two d, 3-CH$_2$), 2.90 and 3.05 (dd and ddd, 5-CH$_2$), 6.74 (d, H-6), 6.80 (dd, H-8), and 7.60 (d, H-9); mass spectrum m/z 229.1 (M + 1).

| | | |
|---|---|---|
| 15 | R$^3$ = Br | 1,6-dibromo-7-hydroxy-3a-methyl- |
| | R$^7$ = Br | 3,3a,4,5-tetrahydro-2H- |
| | R$^{10}$ = CH$_3$ | cyclopenta[α]naphthalen-2-one |

$^1$H NMR (CDCl$_3$, 500 MHz) δ 1.21 (s, CH$_3$), 1.89 and 2.16 (ddd and dd, 4-CH$_2$), 2.44 and 2.60 (two d, 3-CH$_2$), 2.88 and 3.06 (ddd and dd, 5-CH$_2$), 6.10 (s, OH), 7.07 (d, H-8), and 8.46 (d, H-9); mass spectrum m/z 371.0 (M + 1), 373.0 and 375.0.

| | | |
|---|---|---|
| 16 | R$^3$ = CH$_3$ | 6-bromo-7-hydroxy-1,3a-dimethyl- |
| | R$^7$ = Br | 3,3a,4,5-tetrahydro-2H- |
| | R$^{10}$ = CH$_3$ | cyclopenta[α]naphthalen-2-one |

$^1$H NMR (CDCl$_3$, 500 MHz) δ 1.14 (s, 3a-CH$_3$), 1.78 and 2.16 (ddd and dd, 4-CH$_2$), 2.00 (s, 1-CH$_3$), 2.30 and 2.48 (two d, 3-CH$_2$), 2.87 and 3.02 (ddd and dd, 5-CH$_2$), 5.93 (s, OH), 7.03 (d, H-8), and 7.59 (d, H-9); mass spectrum m/z 307.1 (M + 1) and 309.1.

| | | |
|---|---|---|
| 17 | R$^3$ = Br | 1-bromo-3a-ethyl-7-hydroxy-3,3a,4,5- |
| | R$^7$ = H | tetrahydro-2H-cyclopenta[α]naphthalen- |
| | R$^{10}$ = CH$_2$CH$_3$ | 2-one |

-continued

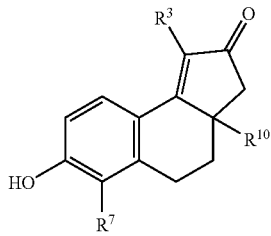

¹H NMR (CDCl₃, 500 MHz) δ 0.82 (t, CH₂CH₃), 1.45 and 1.61 (two dq, CH₂CH₃), 1.86 and 2.17 (ddd and dd, 4-CH₂), 2.25 and 2.65 (two d, 3-CH₂), 2.90 and 3.02 (dd and ddd, 5-CH₂), 6.74 (d, H-6), 6.83 (dd, H-8), and 8.43 (d, H-9); mass spectrum m/z 307.1 (M + 1) and 309.1.

18  R³ = CH₃      3a-ethyl-7-hydroxy-1-methyl-3,3a,4,5-
    R⁷ = H        tetrahydro-2H-cyclopenta[α]naphthalen-
    R¹⁰ = CH₂CH₃  2-one ¹H NMR (CDCl₃, 500 MHz) δ 0.79 (t, CH₂CH₃), 1.37 and 1.57 (two dq, CH₂CH₃), 1.75 and 2.17 (ddd and dd, 4-CH₂), 2.02 (s, 1-CH₃), 2.13 and 2.54 (two d, 3-CH₂), 2.86 and 3.00 (dd and ddd, 5-CH₂), 6.76 (d, H-6), 6.83 (dd, H-8), and 7.57 (d, H-9); mass spectrum m/z 243.2 (M + 1).

19  R³ = Br       1,6-dibromo-3a-ethyl-7-hydroxy-3,3a,4,5-
    R⁷ = Br       tetrahydro-2H-cyclopenta[α]naphthalen-
    R¹⁰ = CH₂CH₃  2-one ¹H NMR (CDCl₃, 500 MHz) δ 0.81 (t, CH₂CH₃), 1.44 and 1.56 (two dq, CH₂CH₃), 1.87 and 2.28 (two ddd, 4-CH₂), 2.27 and 2.66 (two d, 3-CH₂), 2.84 and 3.01 (ddd and dd, 5-CH₂), 6.07 (s, OH), 7.06 (d, H-8), and 8.41 (d, H-9).

20  R³ = Br          1-bromo-7-hydroxy-3a-propyl-3,3a,4,5-
    R⁷ = H           tetrahydro-2H-cyclopenta[α]naphthalen-
    R¹⁰ = CH₂CH₂CH₃  2-one ¹H NMR (CDCl₃, 500 MHz) δ 0.77 (t, CH₂CH₂CH₃), 1.06 and 1.23 (two m, CH₂CH₂CH₃), 1.29 and 1.48 (two dt, CH₂CH₂CH₃), 1.77 and 2.09 (ddd and dd, 4-CH₂), 2.20 and 2.58 (two d, 3-CH₂), 2.82 and 2.95 (dd and ddd, 5-CH₂), 6.64 (d, H-6), 6.75 (dd, H-8), and 8.33 (d, H-9).

21  R³ = CH₃         7-hydroxy-1-methyl-3a-propyl-3,3a,4,5-
    R⁷ = H           tetrahydro-2H-cyclopenta[α]naphthalen-
    R¹⁰ = CH₂CH₂CH₃  2-one ¹H NMR (CDCl₃, 500 MHz) δ 0.81 (t, CH₂CH₂CH₃), 1.04-1.15, 1.23-1.34, and 1.51 (three m, CH₂CH₂CH₃), 1.73 and 2.16 (ddd and dd, 4-CH₂), 2.16 and 2.57 (two d, 3-CH₂), 2.86 and 3.00 (dd and ddd, 5-CH₂), 6.78 (d, H-6), 6.85 (dd, H-8), 7.38 (br s, OH), and 7.57 (d, H-9); mass spectrum m/z 257.1 (M + 1).

22  R³ = Br          1,6-dibromo-7-hydroxy-3a-propyl-
    R⁷ = Br          3,3a,4,5-tetrahydro-2H-
    R¹⁰ = CH₂CH₂CH₃  cyclopenta[α]naphthalen-2-one ¹H NMR (CDCl₃, 500 MHz) δ 0.83 (t, CH₂CH₂CH₃), 1.10 and 1.28 (two m, CH₂CH₂CH₃), 1.35 and 1.50 (two m, CH₂CH₂CH₃), 1.75 and 2.26 (ddd and dd, 4-CH₂), 2.29 and 2.68 (two d, 3-CH₂), 2.84 and 3.01 (dd and ddd, 5-CH₂), 6.16 (s, OH), 7.06 (d, H-8), and 8.40 (d, H-9).

23  R³ = Br       1-bromo-6-chloro-3a-ethyl-7-hydroxy-
    R⁷ = Cl       3,3a,4,5-tetrahydro-2H-
    R¹⁰ = CH₂CH₃  cyclopenta[α]naphthalen-2-one ¹H NMR (CDCl₃, 500 MHz) δ 0.81 (t, CH₂CH₃), 1.44 and 1.53-1.6 (two m, CH₂CH₃), 1.87 and 2.29 (ddd and ddd, 4-CH₂), 2.26 and 2.66 (two d, 3-CH₂), 2.86 and 3.02 (dd and ddd, 5-CH₂), 6.03 (s, OH), 7.06 (d, H-8), and 8.38 (d, H-9) mass spectrum m/z 341.2, 343.2 (M + 1), 345.2

24  R³ = Br          1-bromo-3a-butyl-6-chloro-7-hydroxy-
    R⁷ = Cl          3,3a,4,5-tetrahydro-2H-
    R¹⁰ = CH₂CH₂CH₃  cyclopenta[α]naphthalen-2-one ¹H NMR (CDCl₃, 500 MHz) δ 0.82 (t, CH₂CH₂CH₂CH₃), 1.02-1.10, 1.17-1.3, 1.3-1.38, and 1.47-1.55 (four m, CH₂CH₂CH₂CH₃), 1.85 and 2.27 (ddd and m, 4-CH₂), 2.26 and 2.69 (two d, 3-CH₂), 2.85 and 3.05 (ddd and dd, 5-CH₂), 5.99 (s, OH), 7.06 (d, H-8), and 8.38 (d, H-9).

EXAMPLE 25

The following compounds are prepared using methods analogous to those described in the preceding examples and in the tetrahydrofluorenone patent application WO200182923-A1 (published 8 Nov. 2001):

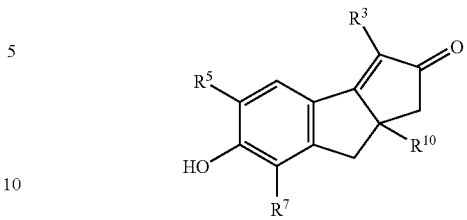

| R³ | R⁵ | R⁷ | R¹⁰ |
|---|---|---|---|
| CH₃ | H | H | CH₂CH₃ |
| CH₂CH₃ | H | H | CH₂CH₃ |
| Cl | H | H | CH₂CH₃ |
| Br | H | H | CH₂CH₃ |
| CN | H | H | CH₂CH₃ |
| CF₃ | H | H | CH₂CH₃ |
| C₆H₅ | H | H | CH₂CH₃ |
| CH₃ | H | H | CH₂CH₂CH₃ |
| CH₂CH₃ | H | H | CH₂CH₂CH₃ |
| Cl | H | H | CH₂CH₂CH₃ |
| CN | H | H | CH₂CH₂CH₃ |
| CF₃ | H | H | CH₂CH₂CH₃ |
| C₆H₅ | H | H | CH₂CH₂CH₃ |
| CH₂CH₃ | H | Cl | CH₂CH₃ |
| Br | H | Cl | CH₂CH₃ |
| Cl | H | Cl | CH₂CH₃ |
| CN | H | Cl | CH₂CH₃ |
| CH₃ | H | Cl | CH₂CH₂CH₃ |
| Br | H | Cl | CH₂CH₂CH₃ |
| Cl | H | Cl | CH₂CH₂CH₃ |
| CN | H | Cl | CH₂CH₂CH₃ |
| CH₃ | F | Cl | CH₂CH₃ |
| CH₂CH₃ | F | Cl | CH₂CH₃ |
|  | F | Cl | CH₂CH₃ |
| Cl | F | Cl | CH₂CH₃ |
| Br | F | Cl | CH₂CH₃ |
| C₆H₅ | F | Cl | CH₂CH₃ |
| CH₃ | F | Cl | CH₂CH₂CH₃ |
| CH₂CH₃ | F | Cl | CH₂CH₂CH₃ |
|  | F | Cl | CH₂CH₂CH₃ |
| Cl | F | Cl | CH₂CH₂CH₃ |
| Br | F | Ci | CH₂CH₂CH₃ |
| C₆H₅ | F | Cl | CH₂CH₂CH₃ |

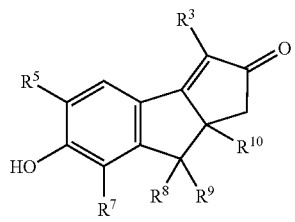

| R³ | R⁵ | R⁷ | R⁸ | R⁹ | R¹⁰ |
|---|---|---|---|---|---|
| CF₃ | H | H | F | Cl | CH₂CH₂CH₃ |
| Br | H | H | H | CH₃ | CH₂CH₂CH₃ |
| Br | F | Cl | H | CH₃ | CH₂CH₂CH₃ |

-continued

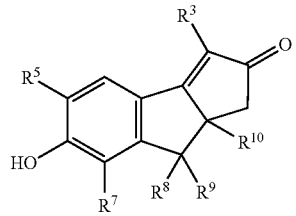

| R³ | R⁵ | R⁷ | R⁸ | R⁹ | R¹⁰ |
|---|---|---|---|---|---|
| CH₃ | H | H | =O | | CH₂CH₂CH₂CH₃ |
| Br | H | H | =O | | CH₂CH₂CH₂CH₃ |
| CH₃ | F | Cl | =O | | CH₂CH₂CH₂CH₃ |
| Br | F | Cl | =O | | CH₂CH₂CH₂CH₃ |
| CF₃ | F | Cl | =O | | CH₂CH₂CH₂CH₃ |

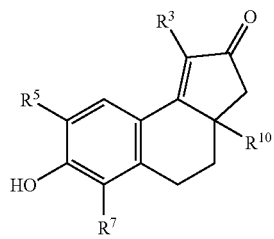

| R³ | R⁵ | R⁷ | R¹⁰ |
|---|---|---|---|
| 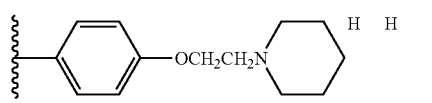 | H | H | CH₂CH₃ |
| CF₃ | H | H | CH₂CH₃ |
| Cl | H | H | CH₂CH₃ |
| I | H | H | CH₂CH₃ |
| CN | H | H | CH₂CH₃ |
| C₆H₅ | H | H | CH₂CH₃ |
| m-(CN)C₆H₄ | H | H | CH₂CH₃ |
| p-(OH)C₆H₄ | H | H | CH₂CH₃ |
|  | H | H | CH₂CH₃ |
| | H | H | CH₂CH₃ |
| CH₂CH₃ | H | H | CH₂CH₂CH₂CH₃ |
|  | H | H | CH₂CH₂CH₂CH₃ |
| CF₃ | H | H | CH₂CH₂CH₂CH₃ |
| Cl | H | H | CH₂CH₂CH₂CH₃ |
| I | H | H | CH₂CH₂CH₂CH₃ |
| CN | H | H | CH₂CH₂CH₂CH₃ |
| C₆H₅ | H | H | CH₂CH₂CH₂CH₃ |
| m-(CN)C₆H₄ | H | H | CH₂CH₂CH₂CH₃ |
| p-(OH)C₆H₄ | H | H | CH₂CH₂CH₂CH₃ |

-continued

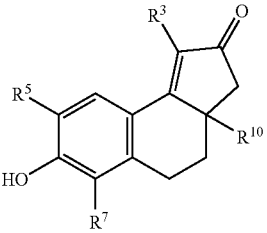

| R³ | R⁵ | R⁷ | R¹⁰ |
|---|---|---|---|
| 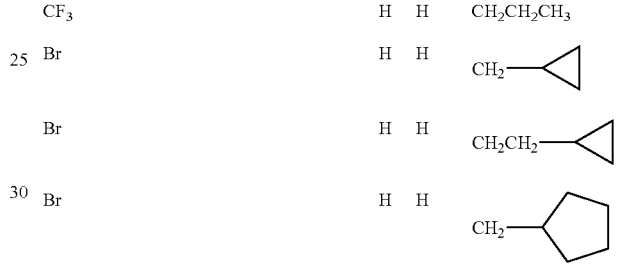 | H | H | CH₂CH₂CH₂CH₃ |
| 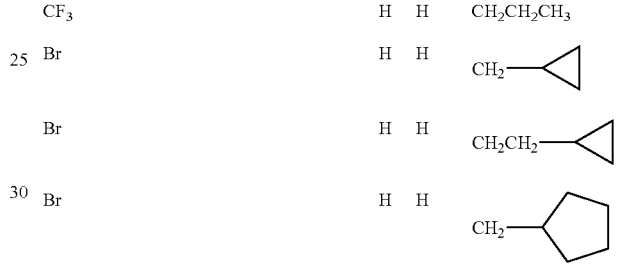 | H | H | CH₂CH₂CH₂CH₃ |
| CF₃ | H | H | CH₂CH₂CH₃ |
| Br | H | H | CH₂-cyclopropyl |
| Br | H | H | CH₂CH₂-cyclopropyl |
| Br | H | H | CH₂-cyclopentyl |
| Br | H | H | CH₂CH₂F |
| CF₃ | H | H | CH₂CH₂F |
| Br | H | H | CH₂CH₂CF₃ |
| Br | H | H | CH₂CH₂CF₂CH₃ |
| CH₃ | H | CH₃ | CH₂CH₃ |
| CH₂CH₃ | H | CH₃ | CH₂CH₃ |
| Cl | H | CH₃ | CH₂CH₃ |
| Br | H | CH₃ | CH₂CH₃ |
| CN | H | CH₃ | CH₂CH₃ |
| CF₃ | H | CH₃ | CH₂CH₃ |
| CH₂CH₃ | H | CH₃ | CH₂CH₂CH₂CH₃ |
| Cl | H | CH₃ | CH₂CH₂CH₂CH₃ |
| Br | H | CH₃ | CH₂CH₂CH₂CH₃ |
| CN | H | CH₃ | CH₂CH₂CH₂CH₃ |
| CF₃ | H | CH₃ | CH₂CH₂CH₂CH₃ |
| CH₃ | H | Cl | CH₂CH₃ |
| CH₂CH₃ | H | Cl | CH₂CH₃ |
| Cl | H | Cl | CH₂CH₃ |
| CN | H | Cl | CH₂CH₃ |
| CF₃ | H | Cl | CH₂CH₃ |
| CH₃ | H | Cl | CH₂CH₂CH₂CH₃ |
| CH₂CH₃ | H | Cl | CH₂CH₂CH₂CH₃ |
| Cl | H | Cl | CH₂CH₂CH₂CH₃ |
| CN | H | Cl | CH₂CH₂CH₂CH₃ |
| CF₃ | H | Cl | CH₂CH₂CH₂CH₃ |
| CH₃ | F | CH₃ | CH₂CH₃ |
| CH₂CH₃ | F | CH₃ | CH₂CH₃ |
| 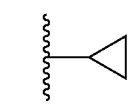 | F | CH₃ | CH₂CH₃ |
| Cl | F | CH₃ | CH₂CH₃ |
| Br | F | CH₃ | CH₂CH₃ |
| CN | F | CH₃ | CH₂CH₃ |
| C₆H₅ | F | CH₃ | CH₂CH₃ |
| m-(CN)C₆H₄ | F | CH₃ | CH₂CH₃ |
| CH₃ | F | CH₃ | CH₂CH₂CH₂CH₃ |
| CH₂CH₃ | F | CH₃ | CH₂CH₂CH₂CH₃ |

-continued

Structure (col 55): tricyclic cyclopentanone fused with aromatic ring bearing R³ (alpha to C=O), R⁵, HO, R⁷, and R¹⁰ at ring junction.

| R³ | R⁵ | R⁷ | R¹⁰ |
|---|---|---|---|
| cyclopropyl | F | CH₃ | CH₂CH₂CH₂CH₃ |
| Cl | F | CH₃ | CH₂CH₂CH₂CH₃ |
| Br | F | CH₃ | CH₂CH₂CH₂CH₃ |
| CN | F | CH₃ | CH₂CH₂CH₂CH₃ |
| C₆H₅ | F | CH₃ | CH₂CH₂CH₂CH₃ |
| m-(CN)C₆H₄ | F | CH₃ | CH₂CH₂CH₂CH₃ |
| CH₃ | F | Cl | CH₂CH₃ |
| CH₂CH₃ | F | Cl | CH₂CH₃ |
| cyclopropyl | F | Cl | CH₂CH₃ |
| Cl | F | Cl | CH₂CH₃ |
| Br | F | Cl | CH₂CH₃ |
| CN | F | Cl | CH₂CH₃ |
| C₆H₅ | F | Cl | CH₂CH₃ |
| m-(CN)C₆H₄ | F | Cl | CH₂CH₃ |
| CH₃ | F | Cl | CH₂CH₂CH₂CH₃ |
| CH₂CH₃ | F | Cl | CH₂CH₂CH₂CH₃ |
| cyclopropyl | F | Cl | CH₂CH₂CH₂CH₃ |
| Cl | F | Cl | CH₂CH₂CH₂CH₃ |
| CN | F | Cl | CH₂CH₂CH₂CH₃ |
| C₆H₅ | F | Cl | CH₂CH₂CH₂CH₃ |
| m-(CN)C₆H₄ | F | Cl | CH₂CH₂CH₂CH₃ |
| Cl | F | Cl | CH₂CH₂F |
| Cl | F | Cl | CH₂CH₂CF₃ |
| Cl | F | Cl | CH₂CH₂CF₂CH₃ |
| Cl | F | Cl | CH₂-cyclopentyl |
| Br | F | Cl | CH₂CH₂F |
| Br | F | Cl | CH₂CH₂CF₃ |
| Br | F | Cl | CH₂CH₂CF₂CH₃ |
| Br | F | Cl | CH₂-cyclopentyl |

Structure (col 56): tetracyclic tetrahydrophenanthrenone with R³, R⁵, HO, R⁷, R¹⁰.

| R³ | R⁵ | R⁷ | R¹⁰ |
|---|---|---|---|
| CH₃ | H | H | CH₂CH₃ |
| CH₂CH₃ | H | H | CH₂CH₃ |
| Cl | H | H | CH₂CH₃ |
| Br | H | H | CH₂CH₃ |
| CN | H | H | CH₂CH₃ |
| CF₃ | H | H | CH₂CH₃ |
| C₆H₅ | H | H | CH₂CH₃ |
| CH₃ | H | H | CH₂CH₂CH₂CH₃ |
| CH₂CH₃ | H | H | CH₂CH₂CH₂CH₃ |
| Cl | H | H | CH₂CH₂CH₂CH₃ |
| CN | H | H | CH₂CH₂CH₂CH₃ |
| CF₃ | H | H | CH₂CH₂CH₂CH₃ |
| C₆H₅ | H | H | CH₂CH₂CH₂CH₃ |
| CH₂CH₃ | H | Cl | CH₂CH₃ |
| Br | H | Cl | CH₂CH₃ |
| Cl | H | Cl | CH₂CH₃ |
| CN | H | Cl | CH₂CH₃ |
| CH₃ | H | Cl | CH₂CH₂CH₂CH₃ |
| Br | H | Cl | CH₂CH₂CH₂CH₃ |
| Cl | H | Cl | CH₂CH₂CH₂CH₃ |
| CN | H | Cl | CH₂CH₂CH₂CH₃ |
| CH₃ | F | Cl | CH₂CH₃ |
| CH₂CH₃ | F | Cl | CH₂CH₃ |
| cyclopropyl | F | Cl | CH₂CH₃ |
| Cl | F | Cl | CH₂CH₃ |
| Br | F | Cl | CH₂CH₃ |
| C₆H₅ | F | Cl | CH₂CH₃ |
| CH₃ | F | Cl | CH₂CH₂CH₂CH₃ |
| CH₂CH₃ | F | Cl | CH₂CH₂CH₂CH₃ |
| cyclopropyl | F | Cl | CH₂CH₂CH₂CH₃ |
| Cl | F | Cl | CH₂CH₂CH₂CH₃ |
| Br | F | Cl | CH₂CH₂CH₂CH₃ |
| C₆H₅ | F | Cl | CH₂CH₂CH₂CH₃ |

Structure: tetrahydrophenanthrenone with R³, R⁵, HO, R⁷, R⁸, R⁹, R¹⁰.

| R³ | R⁵ | R⁷ | R⁸ | R⁹ | R¹⁰ |
|---|---|---|---|---|---|
| CF₃ | H | H | F | Cl | CH₂CH₂CH₂CH₃ |
| Br | H | H | H | CH₃ | CH₂CH₂CH₂CH₃ |

-continued

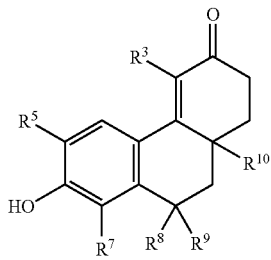

| R³ | R⁵ | R⁷ | R⁸ | R⁹ | R¹⁰ |
|---|---|---|---|---|---|
| Br | F | Cl | H | CH₃ | CH₂CH₂CH₃ |
| CH₃ | H | H | | =O | CH₂CH₂CH₃ |
| Br | H | H | | =O | CH₂CH₂CH₃ |
| CH₃ | F | Cl | | =O | CH₂CH₂CH₃ |
| Br | F | Cl | | =O | CH₂CH₂CH₃ |
| CF₃ | F | Cl | | =O | CH₂CH₂CH₃ |

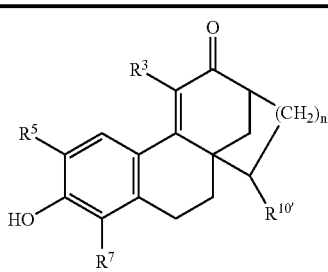

| n | R³ | R⁵ | R⁷ | R¹⁰′ |
|---|---|---|---|---|
| 1 | CH₃ | H | H | H |
| 1 | CH₃ | H | H | CH₃ |
| 1 | CH₃ | H | H | CH₂CH₂CH₃ |
| 1 | Br | H | H | H |
| 1 | Br | H | H | CH₃ |
| 1 | Br | H | H | CH₂CH₂CH₃ |
| 1 | CH₃ | F | Cl | H |
| 1 | CH₃ | F | Cl | CH₃ |
| 1 | CH₃ | F | Cl | CH₂CH₂CH₃ |
| 1 | Br | F | Cl | H |
| 1 | Br | F | Cl | CH₃ |
| 1 | Br | F | Cl | CH₂CH₂CH₃ |
| 2 | CH₃ | H | H | H |
| 2 | Br | H | H | H |
| 2 | CH₃ | F | Cl | H |
| 2 | Br | F | Cl | H |

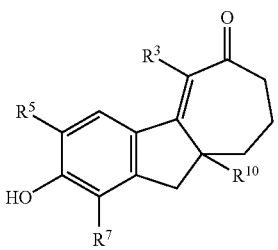

| R³ | R⁵ | R⁷ | R¹⁰ |
|---|---|---|---|
| CH₃ | H | H | CH₂CH₃ |
| CH₂CH₃ | H | H | CH₂CH₃ |
| Cl | H | H | CH₂CH₃ |

-continued

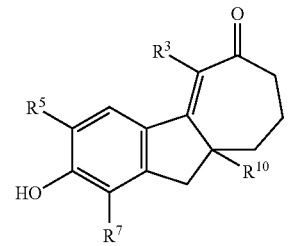

| R³ | R⁵ | R⁷ | R¹⁰ |
|---|---|---|---|
| Br | H | H | CH₂CH₃ |
| CN | H | H | CH₂CH₃ |
| CF₃ | H | H | CH₂CH₃ |
| C₆H₅ | H | H | CH₂CH₃ |
| CH₂CH₃ | H | H | CH₂CH₃ |
| Cl | H | H | CH₂CH₂CH₃ |
| Br | H | H | CH₂CH₂CH₃ |
| CN | H | H | CH₂CH₂CH₃ |
| CF₃ | H | H | CH₂CH₂CH₃ |
| C₆H₅ | H | H | CH₂CH₂CH₃ |
| CH₂CH₃ | H | Cl | CH₂CH₃ |
| Br | H | Cl | CH₂CH₃ |
| Cl | H | Cl | CH₂CH₃ |
| CN | H | Cl | CH₂CH₃ |
| CH₃ | H | Cl | CH₂CH₂CH₃ |
| Br | H | Cl | CH₂CH₂CH₃ |
| Cl | H | Cl | CH₂CH₂CH₃ |
| CN | H | Cl | CH₂CH₂CH₃ |
| CH₃ | F | Cl | CH₂CH₃ |
| CH₂CH₃ | F | Cl | CH₂CH₃ |
| cyclopropyl | F | Cl | CH₂CH₃ |
| Cl | F | Cl | CH₂CH₃ |
| Br | F | Cl | CH₂CH₃ |
| C₆H₅ | F | Cl | CH₂CH₃ |
| CH₃ | F | Cl | CH₂CH₂CH₃ |
| CH₂CH₃ | F | Cl | CH₂CH₂CH₃ |
| cyclopropyl | F | Cl | CH₂CH₂CH₃ |
| Cl | F | Cl | CH₂CH₂CH₃ |
| Br | F | Cl | CH₂CH₂CH₃ |
| C₆H₅ | F | Cl | CH₂CH₂CH₃ |

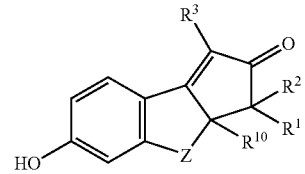

| Z | R¹ | R² | R³ | R¹⁰ |
|---|---|---|---|---|
| CH₂ | CH₂CH₂CH₃ | H | CH₂CH₃ | CH₂CH₂CH₃ |
| CH₂ | OH | H | CH₂CH₃ | CH₂CH₂CH₃ |
| CH₂ | OH | CH₂CH₂CH₃ | CH₂CH₃ | CH₂CH₂CH₃ |
| CH₂ | CH₃ | H | Br | CH₂CH₂CH₃ |
| CH₂ | CH₂CH₂CH₃ | H | Br | CH₂CH₂CH₃ |
| CH₂ | CH₃ | CH₃ | Br | CH₂CH₂CH₃ |

-continued

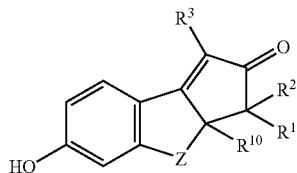

| Z | R1 | R2 | R3 | R10 |
|---|---|---|---|---|
| $CH_2$ | OH | H | Br | $CH_2CH_2CH_2CH_3$ |
| $CH_2$ | OH | $CH_2CH_2CH_3$ | Br | $CH_2CH_2CH_2CH_3$ |
| $CH_2CH_2$ | $CH_2CH_2CH_3$ | H | $CH_2CH_3$ | $CH_2CH_2CH_2CH_3$ |
| $CH_2CH_2$ | OH | H | $CH_2CH_3$ | $CH_2CH_2CH_2CH_3$ |
| $CH_2CH_2$ | OH | $CH_2CH_2CH_3$ | $CH_2CH_3$ | $CH_2CH_2CH_2CH_3$ |
| $CH_2CH_2$ | $CH_3$ | H | Br | $CH_2CH_2CH_2CH_3$ |
| $CH_2CH_2$ | $CH_2CH_2CH_3$ | H | Br | $CH_2CH_2CH_2CH_3$ |
| $CH_2CH_2$ | $CH_3$ | $CH_3$ | Br | $CH_2CH_2CH_2CH_3$ |
| $CH_2CH_2$ | OH | H | Br | $CH_2CH_2CH_2CH_3$ |
| $CH_2CH_2$ | OH | $CH_2CH_2CH_3$ | Br | $CH_2CH_2CH_2CH_3$ |

Estrogen Receptor Binding Assay

The estrogen receptor ligand binding assays are designed as scintillation proximity assays employing the use of tritiated estradiol and recombinant expressed estrogen receptors. The full length recombinant human ER-α and ER-β proteins are produced in a bacculoviral expression system. ER-α or ER-β extracts are diluted 1:400 in phosphate buffered saline containing 6 mM α-monothiolglycerol. 200 μL aliquots of the diluted receptor preparation are added to each well of a 96-well Flashplate. Plates are covered with Saran Wrap and incubated at 4° C. overnight.

The following morning, a 20 ul aliquot of phosphate buffered saline containing 10% bovine serum albumin is added to each well of the 96 well plate and allowed to incubate at 4° C. for 2 hours. Then the plates are washed with 200 ul of buffer containing 20 mM Tris (pH 7.2), 1 mM EDTA, 10% Glycerol, 50 mM KCl, and 6 mM α-monothiolglycerol. To set up the assay in these receptor coated plates, add 178 ul of the same buffer to each well of the 96 well plate. Then add 20 ul of a 10 nM solution of $^3$H-estradiol to each well of the plate.

Test compounds are evaluated over a range of concentrations from 0.01 nM to 1000 nM. The test compound stock solutions should be made in 100% DMSO at 100× the final concentration desired for testing in the assay. The amount of DMSO in the test wells of the 96 well plate should not exceed 1%. The final addition to the assay plate is a 2 ul aliquot of the test compound which has been made up in 100% DMSO. Seal the plates and allow them to equilibrate at room temperature for 3 hours. Count the plates in a scintillation counter equipped for counting 96 well plates.

The compounds of Examples 1-23 exhibit binding affinities to the estrogen receptor α-subtype in the range of $IC_{50}$=75 to >10000 nm, and to the estrogen receptor β-subtype in the range of $IC_{50}$=5 to 250 nm.

Pharmaceutical Composition

As a specific embodiment of this invention, 25 mg of compound of Example 5, is formulated with sufficient finely divided lactose to provide a total amount of 580 to 590 mg to fill a size 0, hard-gelatin capsule.

What is claimed is:
1. A compound of the formula:

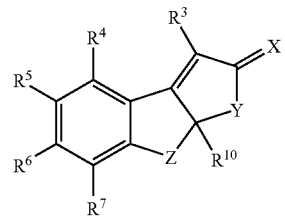

wherein X is O;
Y is $CR^1R^2$, $CH_2CH_2CR^1R^2$;
Z is $CH_2$ or $CH_2CH_2$;
$R^1$ is hydrogen, $C_{1-3}$alkyl;
$R^2$ is hydrogen, hydroxy or $C_1$;
$R^3$ is chloro, bromo, cyano, $C_{1-10}$ alkyl, $C_{3-7}$cycloalkyl, aryl or heteroaryl, wherein said alkyl, cycloalkyl, aryl and heteroaryl groups are either unsubstituted or independently substituted with 1, 2 or 3 groups selected from fluoro, chloro, cyano, $OR^a$, $LR^d$ or $MLR^d$;
$R^4$ is hydrogen;
$R^5$ is hydrogen or fluoro;
$R^6$ is $OR^a$ or $O(C=O)R^c$;
$R^7$ is hydrogen, chloro or methyl;
$R^8$ and $R^9$ are each hydrogen;
  or $R^8$ and $R^9$, when taken together with the carbon atom to which they are attached, form a carbonyl group;
$R^{10}$ is $C_{1-10}$alkyl, or (cycloalkyl)alkyl wherein said alkyl and (cycloalkyl)alkyl groups are unsubstituted or substituted with 1-5 fluoro;
$R^a$ is hydrogen, $C_{1-10}$-alkyl and phenyl, wherein said alkyl group is optionally substituted with a group selected from hydroxy, amino, $O(C_{1-4}$alkyl), $NH(C_{1-4}$alkyl), $N(C_{1-4}$alkyl)$_2$, phenyl, or 1-5 fluoro, and wherein said phenyl groups can either be unsubstituted or substituted with 1-3 substituents independently selected from $C_{1-4}$alkyl, OH, $O(C_{1-4}$alkyl), $NH_2$, $NH(C_{1-4}$alkyl), $N(C_{1-4}$alkyl)$_2$, halo, CN, $NO_2$, $CO_2H$, $CO_2(C_{1-4}$alkyl), $C(O)H$ or $C(O)(C_{1-4}$alkyl);
$R^b$ is hydrogen, $C_{1-10}$alkyl, benzyl or phenyl, wherein said phenyl group can either be unsubstituted or substituted with 1-3 substituents independently selected from $C_{1-4}$alkyl, OH, $O(C_{1-4}$alkyl), $NH_2$, $NH(C_{1-4}$alkyl), $N(C_{1-4}$alkyl)$_2$, halo, CN, $NO_2$, $CO_2H$, $CO_2(C_{1-4}$alkyl), $C(O)H$ or $C(O)(C_{1-4}$alkyl);
$R^c$ is hydrogen, $C_{1-10}$alkyl or phenyl, wherein said phenyl group can either be unsubstituted or substituted with 1-3 substituents independently selected from $C_{1-4}$alkyl, OH, $O(C_{1-4}$alkyl), $NH_2$, $NH(C_{1-4}$alkyl), $N(C_{1-4}$alkyl)$_2$, halo, CN, $NO_2$, $CO_2H$, $CO_2(C_{1-4}$alkyl), $C(O)H$ or $C(O)(C_{1-4}$ alkyl);
  or $R^a$ and $R^c$, whether or not on the same atom, can be taken together with any attached and intervening atoms to form a 4-7 membered ring;
$R^d$ is $NR^bR^c$, $OR^a$, $CO_2R^a$, $O(C=O)R^a$, CN, $NR^c(C=O)R^b$, $CONR^aR^c$, $SO_2NR^aR^c$ or a 4-9 membered mono- or bi-cyclic N-heterocycloalkyl ring that can be optionally substituted with 1-3 $C_{1-3}$ alkyl and can be optionally interrupted by O, S, $NR^c$, or C=O;
$R^e$ is hydrogen, $C_{1-6}$alkyl, $C_{2-6}$alkenyl, phenyl or phenylalkyl, wherein said alkyl, alkenyl, or phenyl group can either be unsubstituted or substituted with 1-3 substituents independently selected from $C_{1-3}$alkyl, OH, $O(C_{1-4}$ alkyl), $NH_2$, $NH(C_{1-4}alkyl)$, $N(C_{1-4}alkyl)_2$, halo, CN, $NO_2$, $CO_2H$, $CO_2(C_{1-4}alkyl)$, $C(O)H$ or $C(O)(C_{1-4}alkyl)$;

L is $CR^bR^c$, $C_{2-6}$ alkylene or $C_{2-6}$ alkenylene, wherein said alkylene and alkenylene linkers can be optionally interrupted by O, S, or $NR^c$;

M is O, S, $NR^c$, C=O, O(C=O), (C=O)O, $NR^c$(C=O) or (C=O)$NR^c$;

or a pharmaceutically acceptable salt thereof.

2. The compound of claim 1 wherein;

Y is $CH_2$ or $CH_2CH_2CH_2$;

$R^1$ is hydrogen;

$R^2$ is hydrogen;

$R^3$ is chloro, bromo, cyano, methyl, ethyl, trifluoromethyl, cyclopropyl, phenyl, furyl or thienyl;

$R^6$ is hydroxy;

$R^8$ and $R^9$ are each hydrogen;

an or a pharmaceutically acceptable salt thereof.

3. The compound of claim 1 selected from the group consisting of:

3-bromo-8a-butyl-6-hydroxy-8,8a-dihydrocyclopenta[a]inden-2(1H)-one;

(rac)-(1S,8aR)-3-bromo-8a-butyl-6-hydroxy-1-propyl-8,8a-dihydrocyclopenta[a]inden-2(1H)-one;

1,3a-diethyl-7-hydroxy-3,3a,4,5-tetrahydro-2H-cyclopenta[a]naphthalen-2-one;

3a-butyl-7-hydroxy-3,3a,4,5-tetrahydro-2H-cyclopenta[a]naphthalen-2-one;

1,6-dibromo-3a-butyl-7-hydroxy-3,3a,4,5-tetrahydro-2H-cyclopenta[a]naphthalen-2-one;

1-bromo-3a-butyl-7-hydroxy-3,3a,4,5-tetrahydro-2H-cyclopenta[a]naphthalen-2-one;

6-bromo-3a-butyl-7-hydroxy-1-methyl-3,3a,4,5-tetrahydro-2H-cyclopenta[a]naphthalen-2-one;

3a-butyl-7-hydroxy-1,6-dimethyl-3,3a,4,5-tetrahydro-2H-cyclopenta[a]naphthalen-2-one;

3a-butyl-7-hydroxy-1-methyl-3,3a,4,5-tetrahydro-2H-cyclopenta[a]naphthalen-2-one;

1-bromo-3a-butyl-6-chloro-8-fluoro-7-hydroxy-3,3a,4,5-tetrahydro-2H-cyclopenta[a]naphthalen-2-one;

10a-butyl-7-hydroxy-1,9,10,10a-tetrahydro-3(2H)-phenanthrenone;

4-bromo-10a-butyl-7-hydroxy-1,9,10,10a-tetrahydro-3(2H)-phenanthrenone;

9a-butyl-2-hydroxy-5-methyl-8,9,9a,10-tetrahydrobenzo[a]azulen-6(7H)-one;

1-bromo-7-hydroxy-3a-methyl-3,3a,4,5-tetrahydro-2H-cyclopenta[a]naphthalen-2-one;

7-hydroxy-1,3a-dimethyl-3,3a,4,5-tetrahydro-2H-cyclopenta[a]naphthalen-2-one;

1,6-dibromo-7-hydroxy-3a-methyl-3,3a,4,5-tetrahydro-2H-cyclopenta[a]naphthalen-2-one;

6-bromo-7-hydroxy-1,3a-dimethyl-3,3a,4,5-tetrahydro-2H-cyclopenta[a]naphthalen-2-one;

1-bromo-3a-ethyl-7-hydroxy-3,3a,4,5-tetrahydro-2H-cyclopenta[a]naphthalen-2-one;

3a-ethyl-7-hydroxy-1-methyl-3,3a,4,5-tetrahydro-2H-cyclopenta[a]naphthalen-2-one;

1,6-dibromo-3a-ethyl-7-hydroxy-3,3a,4,5-tetrahydro-2H-cyclopenta[a]naphthalen-2-one;

1-bromo-7-hydroxy-3a-propyl-3,3a,4,5-tetrahydro-2H-cyclopenta[a]naphthalen-2-one;

7-hydroxy-1-methyl-3a-propyl-3,3a,4,5-tetrahydro-2H-cyclopenta[a]naphthalen-2-one;

1,6-dibromo-7-hydroxy-3a-propyl-3,3a,4,5-tetrahydro-2H-cyclopenta[a]naphthalen-2-one;

1-bromo-6-chloro-3a-ethyl-7-hydroxy-3,3a,4,5-tetrahydro-2H-cyclopenta[a]naphthalen-2-one;

1-bromo-3a-butyl-6-chloro-7-hydroxy-3,3a,4,5-tetrahydro-2H-cyclopenta[a]naphthalen-2-one;

and the pharmaceutically acceptable salts thereof.

4. A pharmaceutical composition comprising a compound according to claim 1 and a pharmaceutically acceptable carrier.

5. A pharmaceutical composition made by combining a compound according to claim 1 and a pharmaceutically acceptable carrier.

6. A process for making a pharmaceutical composition comprising combining a compound according to claim 1 and a pharmaceutically acceptable carrier.

* * * * *